(12) United States Patent
Beyar et al.

(10) Patent No.: US 9,101,417 B2
(45) Date of Patent: Aug. 11, 2015

(54) COMPOSITE MATERIAL BONE IMPLANT

(71) Applicant: Carbofix Orthopedics Ltd., Herzlia Pituach (IL)

(72) Inventors: Mordechay Beyar, Caesarea (IL); Oren Globerman, Kfar-Shemaryahu (IL); Elad Einav, Zikhron-Yaakov (IL); Hila Wachsler-Avrahami, Tel-Aviv (IL)

(73) Assignee: Carbofix Orthopedics Ltd., Herzlia Pituach (IL)

( * ) Notice: Subject to any disclaimer, the term of this patent is extended or adjusted under 35 U.S.C. 154(b) by 0 days.

(21) Appl. No.: 14/246,161

(22) Filed: Apr. 7, 2014

(65) Prior Publication Data

US 2014/0222001 A1    Aug. 7, 2014

Related U.S. Application Data

(62) Division of application No. 13/144,938, filed as application No. PCT/IB2010/050225 on Jan. 18, 2010, now Pat. No. 8,709,055.

(60) Provisional application No. 61/213,991, filed on Aug. 6, 2009, provisional application No. 61/205,160, filed on Jan. 16, 2009.

(51) Int. Cl.
*A61B 17/72* (2006.01)
*A61B 17/16* (2006.01)
*A61B 17/74* (2006.01)
*A61B 17/80* (2006.01)
(Continued)

(52) U.S. Cl.
CPC ......... *A61B 17/7208* (2013.01); *A61B 17/1631* (2013.01); *A61B 17/72* (2013.01); *A61B 17/744* (2013.01); *A61B 17/80* (2013.01); *A61B 17/866* (2013.01); *A61B 17/8625* (2013.01); *A61B 17/1725* (2013.01); *A61B 17/7225* (2013.01); *A61B 17/7241* (2013.01); *A61B 17/8052* (2013.01); *A61B 17/864* (2013.01); *A61B 17/8872* (2013.01); *A61B 17/92* (2013.01); *A61B 19/54* (2013.01); *A61B 2017/00831* (2013.01)

(58) Field of Classification Search
CPC .................................................. A61B 17/7208
USPC ........................................... 606/62, 300–331
See application file for complete search history.

(56) References Cited

U.S. PATENT DOCUMENTS 3,630,253 A    12/1971  Sherman
4,058,581 A    11/1977  Park
(Continued)

FOREIGN PATENT DOCUMENTS

CN    1170380    1/1998
CN    1367669    9/2002
(Continued)

OTHER PUBLICATIONS

Notice of Reason for Rejection Dated Jun. 3, 2014 From the Japanese Patent Office Re. Application No. 2011-545832 and Its Translation Into English.
(Continued)

*Primary Examiner* — Christopher Beccia

(57) ABSTRACT

A composite bone implant. In some embodiments, one or more features are provided, such as markers for passageways, axial engagement of bone screws, sliding support of bone screws and/or a cannulated channel for a guide wire.

17 Claims, 22 Drawing Sheets

(51) Int. Cl.
  *A61B 17/86* (2006.01)
  *A61B 17/17* (2006.01)
  *A61B 17/88* (2006.01)
  *A61B 17/92* (2006.01)
  *A61B 19/00* (2006.01)
  *A61B 17/00* (2006.01)

(56) References Cited

U.S. PATENT DOCUMENTS

| | | |
|---|---|---|
| 4,220,187 A | 9/1980 | Holmes |
| 4,667,664 A | 5/1987 | Taylor et al. |
| 4,718,801 A | 1/1988 | Berecz |
| 4,750,905 A | 6/1988 | Koeneman et al. |
| 4,824,314 A | 4/1989 | Stencel |
| 4,863,330 A | 9/1989 | Olez et al. |
| 4,978,360 A | 12/1990 | Devanathan |
| 4,988,350 A | 1/1991 | Herzberg |
| 5,009,664 A | 4/1991 | Sievers |
| 5,041,113 A | 8/1991 | Biedermann et al. |
| 5,060,635 A | 10/1991 | Steur et al. |
| 5,064,439 A | 11/1991 | Chang et al. |
| 5,181,930 A | 1/1993 | Dumbleton et al. |
| 5,192,330 A | 3/1993 | Chang et al. |
| 5,197,966 A | 3/1993 | Sommerkamp |
| 5,292,215 A | 3/1994 | Roberts, III |
| 5,397,358 A | 3/1995 | Wenner et al. |
| 5,522,817 A | 6/1996 | Sander et al. |
| 5,824,079 A | 10/1998 | Siegler et al. |
| 5,879,352 A | 3/1999 | Filoso et al. |
| 5,961,524 A | 10/1999 | Crombie |
| 6,030,389 A | 2/2000 | Wagner et al. |
| 6,206,881 B1 | 3/2001 | Frigg et al. |
| 6,471,707 B1 | 10/2002 | Miller et al. |
| 6,605,090 B1 | 8/2003 | Trieu et al. |
| 6,692,498 B1 | 2/2004 | Niiranen et al. |
| 6,730,091 B1 | 5/2004 | Pfefferle et al. |
| 6,916,321 B2 | 7/2005 | TenHuisen et al. |
| 6,921,402 B2 | 7/2005 | Contiliano et al. |
| 7,419,714 B1 | 9/2008 | Magerl et al. |
| 7,785,325 B1 | 8/2010 | Milbank |
| 7,896,599 B2 | 3/2011 | Stephen et al. |
| 7,914,244 B2 | 3/2011 | Bubulka et al. |
| 8,323,321 B2 | 12/2012 | Gradl |
| 2002/0029043 A1 | 3/2002 | Ahrens et al. |
| 2002/0156473 A1 | 10/2002 | Bramlet et al. |
| 2003/0057590 A1 | 3/2003 | Loher et al. |
| 2004/0073218 A1 | 4/2004 | Dahners |
| 2004/0260291 A1 | 12/2004 | Jensen |
| 2005/0131413 A1 | 6/2005 | O'Driscoll et al. |
| 2005/0177153 A1 | 8/2005 | Guzman et al. |
| 2005/0192578 A1 | 9/2005 | Horst |
| 2005/0234457 A1 | 10/2005 | James et al. |
| 2006/0004431 A1 | 1/2006 | Fuller et al. |
| 2006/0009771 A1 | 1/2006 | Orbay et al. |
| 2006/0041261 A1 | 2/2006 | Osypka |
| 2006/0079900 A1 | 4/2006 | Mathieu et al. |
| 2006/0116678 A1 | 6/2006 | Impellizzeri |
| 2006/0195085 A1 | 8/2006 | Happonen et al. |
| 2006/0200142 A1* | 9/2006 | Sohngen et al. ............... 606/62 |
| 2006/0235400 A1 | 10/2006 | Schneider |
| 2006/0259039 A1 | 11/2006 | Pitkanen et al. |
| 2006/0264948 A1 | 11/2006 | Williams |
| 2007/0083207 A1 | 4/2007 | Ziolo et al. |
| 2007/0110544 A1 | 5/2007 | Friedrich et al. |
| 2007/0162018 A1 | 7/2007 | Jensen et al. |
| 2007/0173843 A1 | 7/2007 | Matityahu |
| 2007/0233105 A1 | 10/2007 | Nelson et al. |
| 2007/0260244 A1 | 11/2007 | Wolter |
| 2008/0046091 A1 | 2/2008 | Weiss et al. |
| 2008/0140130 A1 | 6/2008 | Chan et al. |
| 2008/0195157 A1 | 8/2008 | Orschler et al. |
| 2008/0208259 A1 | 8/2008 | Gilbert et al. |
| 2008/0234752 A1 | 9/2008 | Dahners |
| 2008/0234762 A1 | 9/2008 | Forstein et al. |
| 2009/0018588 A1 | 1/2009 | Eckhof et al. |
| 2009/0088807 A1 | 4/2009 | Castaneda et al. |
| 2009/0228008 A1 | 9/2009 | Justin et al. |
| 2009/0228048 A1 | 9/2009 | Duncan et al. |
| 2009/0248089 A1 | 10/2009 | Jacofsky et al. |
| 2009/0312803 A1 | 12/2009 | Austin et al. |
| 2010/0016858 A1 | 1/2010 | Michel |
| 2010/0042215 A1 | 2/2010 | Stalcup et al. |
| 2010/0094423 A1 | 4/2010 | Foley et al. |
| 2010/0100134 A1 | 4/2010 | Mocanu |
| 2010/0234847 A1 | 9/2010 | Impellizzeri |
| 2010/0312286 A1 | 12/2010 | Dell'Oca |
| 2011/0015682 A1 | 1/2011 | Lewis et al. |
| 2011/0218570 A1 | 9/2011 | Felix et al. |
| 2011/0224737 A1 | 9/2011 | Lewis et al. |
| 2011/0282395 A1 | 11/2011 | Beyar et al. |
| 2011/0288598 A1 | 11/2011 | Moed et al. |
| 2012/0059376 A1* | 3/2012 | Rains et al. ............... 606/62 |
| 2012/0083847 A1 | 4/2012 | Huebner et al. |
| 2012/0136396 A1 | 5/2012 | Baker et al. |
| 2012/0203285 A1 | 8/2012 | Rotini et al. |
| 2012/0283790 A1 | 11/2012 | Meyer, III |
| 2012/0330361 A1 | 12/2012 | Gepstein |
| 2013/0079829 A1 | 3/2013 | Globerman et al. |
| 2013/0184765 A1 | 7/2013 | Beyar et al. |
| 2013/0218214 A1 | 8/2013 | Beyar et al. |
| 2013/0237813 A1 | 9/2013 | Beyar et al. |
| 2013/0261675 A1 | 10/2013 | Fritzinger |
| 2013/0296863 A1 | 11/2013 | Globerman et al. |
| 2013/0296952 A1 | 11/2013 | Globerman et al. |
| 2013/0325007 A1 | 12/2013 | Beyar et al. |

FOREIGN PATENT DOCUMENTS

| | | | |
|---|---|---|---|
| CN | 1482890 | 3/2004 | |
| CN | 1586416 | 3/2005 | |
| CN | 2746884 | 12/2005 | |
| CN | 1819799 | 8/2006 | |
| CN | 101304695 | 11/2008 | |
| DE | 4343117 | 6/1995 | |
| EP | 1042989 | 10/2000 | |
| EP | 1598028 | 11/2005 | |
| EP | 1733704 | 12/2006 | |
| EP | 1779796 | 5/2007 | |
| EP | 1857066 | 11/2007 | |
| EP | 2198792 | 6/2010 | |
| EP | 2292176 | 3/2011 | |
| FR | 2555902 | 6/1985 | |
| FR | 2646767 | 11/1990 | |
| FR | 2829378 | 3/2003 | |
| GB | 2442706 | 4/2008 | |
| JP | 02-198550 | 8/1990 | |
| JP | 05-000157 | 1/1993 | |
| JP | 05-092019 | 4/1993 | |
| JP | 06-500945 | 2/1994 | |
| JP | 2002-536048 | 10/2002 | |
| JP | 2007-125387 | 5/2007 | |
| JP | 2008-036094 | 2/2008 | |
| WO | WO 92/18068 | 10/1992 | |
| WO | WO 93/13713 | 7/1993 | |
| WO | WO 94/07425 | 4/1994 | |
| WO | WO 96/02203 | 2/1996 | |
| WO | WO 96/09014 | 3/1996 | |
| WO | WO 9609014 A1 * | 3/1996 | ............ A61B 19/00 |
| WO | WO 96/19336 | 6/1996 | |
| WO | WO 01/15637 | 3/2001 | |
| WO | WO 2006/090226 | 8/2006 | |
| WO | WO 2007/009123 | 1/2007 | |
| WO | WO 2007/010671 | 1/2007 | |
| WO | WO 2007/035772 | 3/2007 | |
| WO | WO 2008/033742 | 3/2008 | |
| WO | WO 2008/064346 | 5/2008 | |
| WO | WO 2008/092192 | 8/2008 | |
| WO | WO 2009/002890 | 12/2008 | |
| WO | WO 2009/143374 | 11/2009 | |
| WO | WO 2009/152270 | 12/2009 | |
| WO | WO 2009/152272 | 12/2009 | |
| WO | WO 2010/045473 | 4/2010 | |
| WO | WO 2010/082183 | 7/2010 | |

(56) References Cited

FOREIGN PATENT DOCUMENTS

| WO | WO 2011/042407 | 4/2011 |
|----|----------------|--------|
| WO | WO 2011/154891 | 12/2011 |
| WO | WO 2012/107913 | 8/2012 |

OTHER PUBLICATIONS

Applicant-Initiated Interview Summary Dated Oct. 17, 2013 From the US Patent and Trademark Office Re. U.S. Appl. No. 13/144,938.
Communication Pursuant to Article 94(3) EPC Dated Jul. 2, 2013 From the European Patent Office Re. Application No. 10702750.0.
Communication Pursuant to Rules 70(2) and 70a(2) EPC and Reference to Rule 39(1) EPC Dated Jul. 22, 2013 From the European Patent Office Re. Application No. 13151490.3.
Communication Relating to the Results of the Partial International Search Dated May 17, 2010 From the International Searching Authority Re.: Application No. PCT/IB2010/050225.
Communication Relating to the Results of the Partial International Search Dated May 29, 2012 From the International Searching Authority Re. Application No. PCT/IB2012/050645.
Communication Relating to the Results of the Partial International Search Dated Sep. 29, 2011 From the International Searching Authority Re. Application No. PCT/IB2011/052468.
Corrected Notice of Allowability Dated Feb. 11, 2014 From the US Patent and Trademark Office Re. U.S. Appl. No. 13/144,938.
Corrected Notice of Allowability Dated Feb. 14, 2014 From the US Patent and Trademark Office Re. U.S. Appl. No. 13/144,938.
European Search Report and the Written Opinion Dated Apr. 18, 2013 From the European Patent Office Re. Application No. 13151490.3.
International Preliminary Report on Patentability Dated Dec. 20, 2012 From the International Bureau of WIPO Re. Application No. PCT/IB2011/052468.
International Preliminary Report on Patentability Dated Aug. 22, 2013 From the International Bureau of WIPO Re. Application No. PCT/IB2012/050645.
International Preliminary Report on Patentability Dated Jul. 28, 2011 From the International Bureau of WIPO Re. Application No. PCT/IB2010/050225.
International Search Report and the Written Opinion Dated Nov. 10, 2010 From the International Searching Authority Re: Application No. PCT/IB2010/050225.
International Search Report and the Written Opinion Dated Aug. 24, 2012 From the International Searching Authority Re: Application No. PCT/IB2010/050225.
International Search Report and the Written Opinion Dated Dec. 29, 2011 From the International Searching Authority Re. Application No. PCT/IB2011/052468.
Notice of Allowance Dated Dec. 11, 2013 From the US Patent and Trademark Office Re. U.S. Appl. No. 13/144,938.
Notice of Reason for Rejection Dated Nov. 15, 2013 From the Japanese Patent Office Re. Application No. 2011-545832 and Its Translation Into English.
Notification of Office Action Dated Mar. 7, 2014 From the State Intellectual Property Office of the People's Republic of China Re. Application No. 201080012276.1 and Its Translation Into English.
Notification of Office Action Dated Oct. 18, 2013 From the State Intellectual Property Office of the People's Republic of China Re. Application No. 201080012276.1 and Its Translation Into English.
Official Action Dated Jan. 27, 2014 From the US Patent and Trademark Office Re. U.S. Appl. No. 13/935,501.
Official Action Dated Jun. 27, 2013 From the US Patent and Trademark Office Re. U.S. Appl. No. 13/144,938.
Restriction Official Action Dated Mar. 22, 2013 From the US Patent and Trademark Office Re. U.S. Appl. No. 13/144,938.
Translation of Notification of Office Action Dated Apr. 12, 2013 From the State Intellectual Property Office of the People's Republic of China Re. Application No. 201080012276.1.
Translation of Search Report Dated Apr. 12, 2013 From the State Intellectual Property Office of the People's Republic of China Re. Application No. 201080012276.1.
Translation of Search Report Dated Oct. 18, 2013 From the State Intellectual Property Office of the People's Republic of China Re. Application No. 201080012276.1.
Office Action Dated Apr. 2, 2014 From the Israel Patent Office Re. Application No. 214105 and Its Translation Into English.
Official Action Dated Jul. 11, 2014 From the US Patent and Trademark Office Re. U.S. Appl. No. 13/935,501.
Communication Pursuant to Article 94(3) EPC Dated Nov. 19, 2014 From the European Patent Office Re. Application No. 10702750.0.
Official Action Dated Dec. 19, 2014 From the US Patent and Trademark Office Re. U.S. Appl. No. 13/742,462. (Part I).
Official Action Dated Dec. 19, 2014 From the US Patent and Trademark Office Re. U.S. Appl. No. 13/742,462. (Part II).
Official Action Dated Dec. 23, 2014 From the US Patent and Trademark Office Re. U.S. Appl. No. 13/935,501.
Official Action Dated Nov. 10, 2014 From the US Patent and Trademark Office Re. U.S. Appl. No. 13/702,334.
Notification of Office Action Dated Oct. 29, 2014 From the State Intellectual Property Office of the People's Republic of China Re. Application No. 201180038951.2 and Its Translation Into English.
Search Report Dated Oct. 29, 2014 From the State Intellectual Property Office of the People's Republic of China Re. Application No. 201180038951.2 and Its Translation Into English.
Applicant-Initiated Interview Summary Dated Nov. 21, 2014 From the US Patent and Trademark Office Re. U.S. Appl. No. 13/935,497.
Official Action Dated Dec. 19, 2014 From the US Patent and Trademark Office Re. U.S. Appl. No. 13/935,497.
Applicant-Initiated Interview Summary Dated Oct. 8, 2014 From the US Patent and Trademark Office Re. U.S. Appl. No. 13/935,501.
Office Action Dated Aug. 10, 2014 From the Israel Patent Office Re. Application No. 214105 and Its Translation Into English.
Communication Pursuant to Article 94(30 EPC Dated Jul. 11, 2014 From the European Patent Office Re. Application No. 13151490.3.
Restriction Official Action Dated Aug. 1, 2014 From the US Patent and Tradmark Office Re. U.S. Appl. No. 13/742,462.
Official Action Dated Aug. 5, 2014 From the US Patent and Trademark Office Re. U.S. Appl. No. 13/935,497.
Official Decision of Rejection Dated Mar. 3, 2015 From the Japanese Patent Office Re. Application No. 2011-545832 and Its Translation Into English.

\* cited by examiner

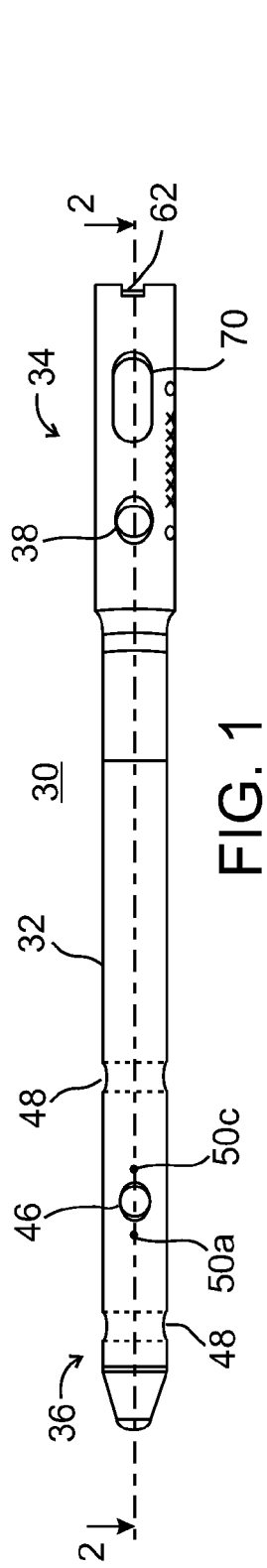
FIG. 1
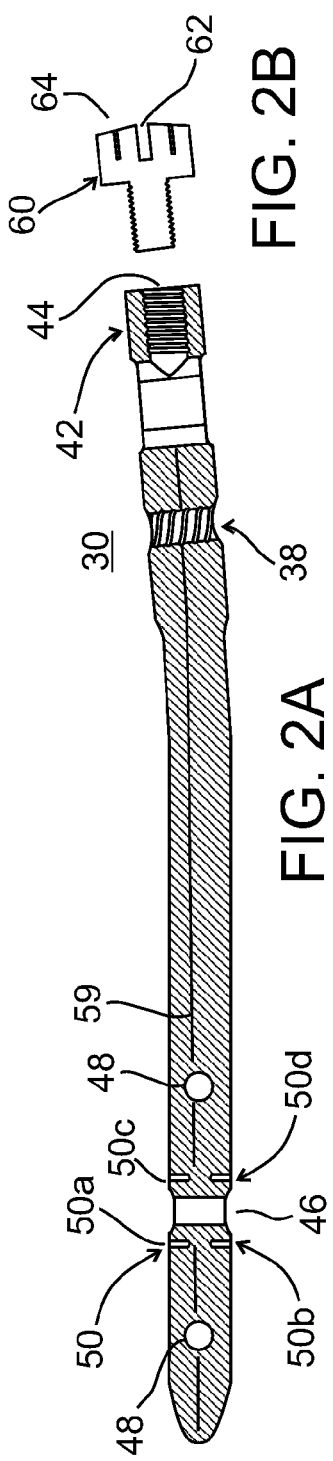
FIG. 2A
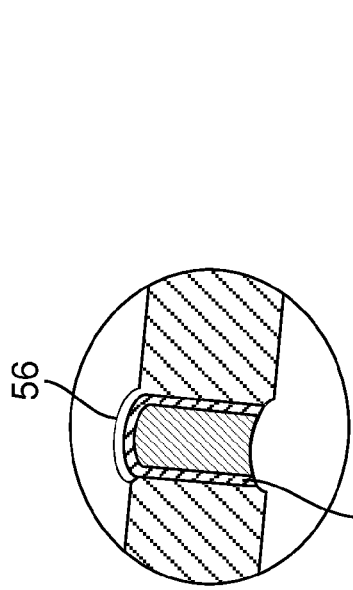
FIG. 2B
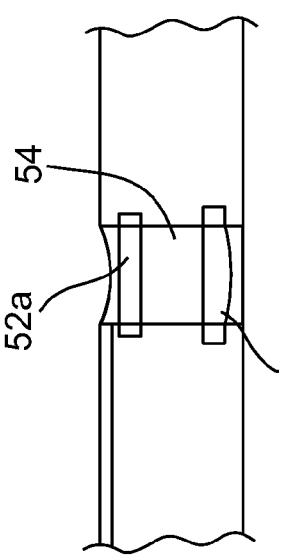
FIG. 3A
FIG. 3B

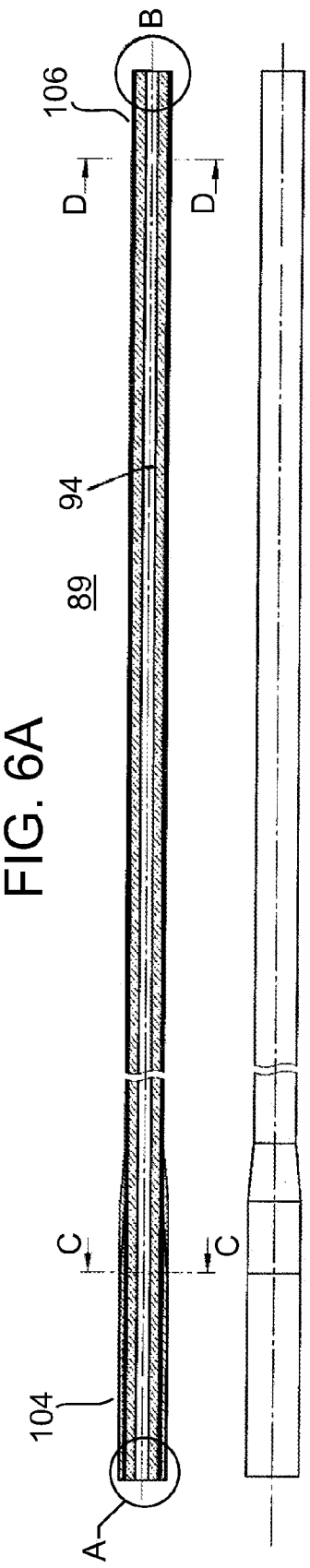
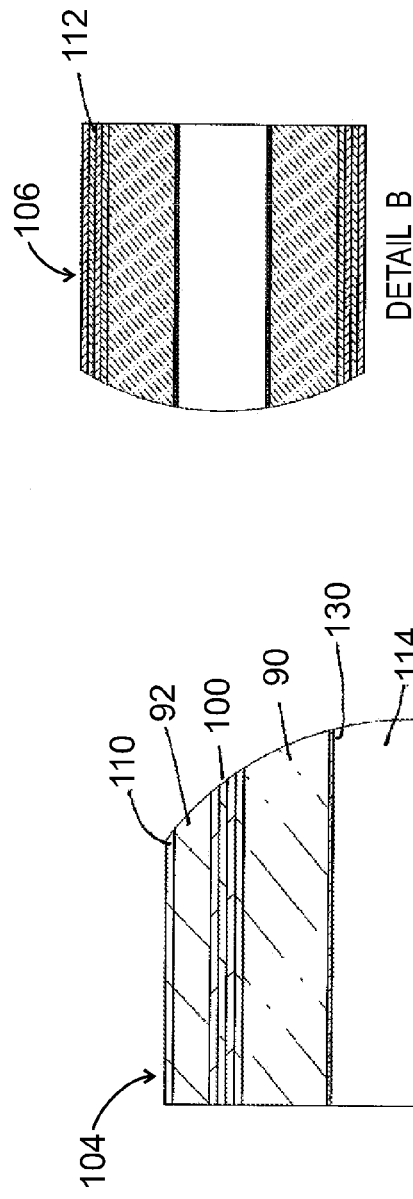
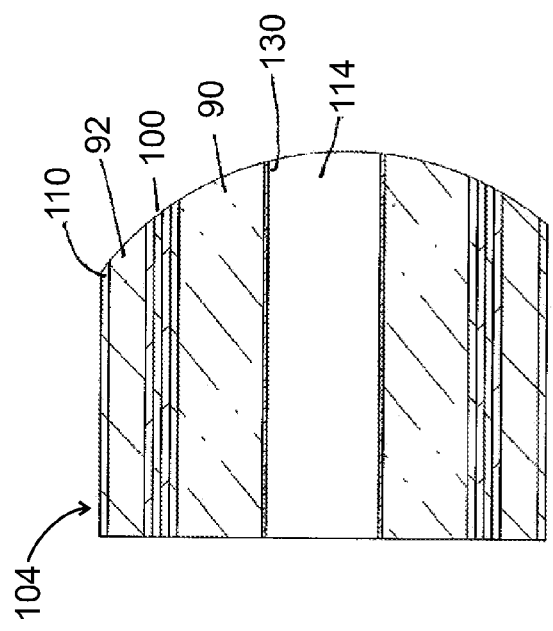
FIG. 6A
FIG. 6B
DETAIL A
FIG. 6C
DETAIL B

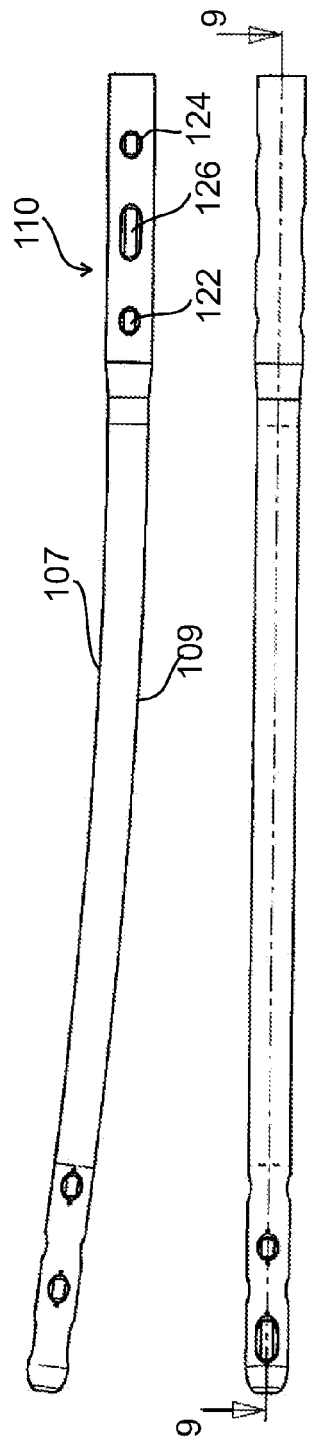
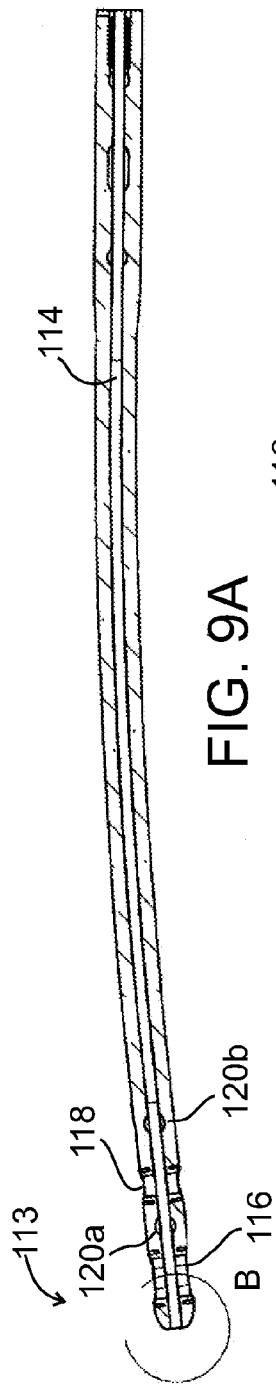
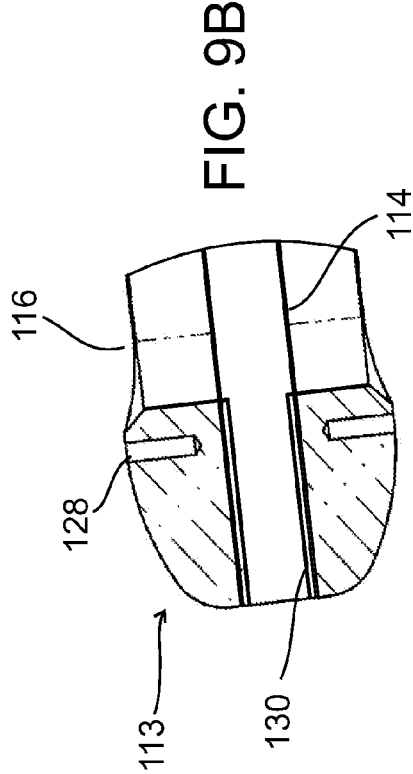

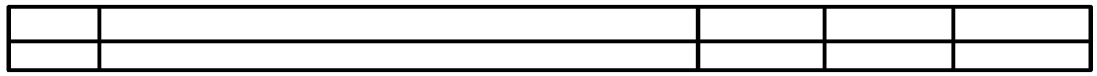
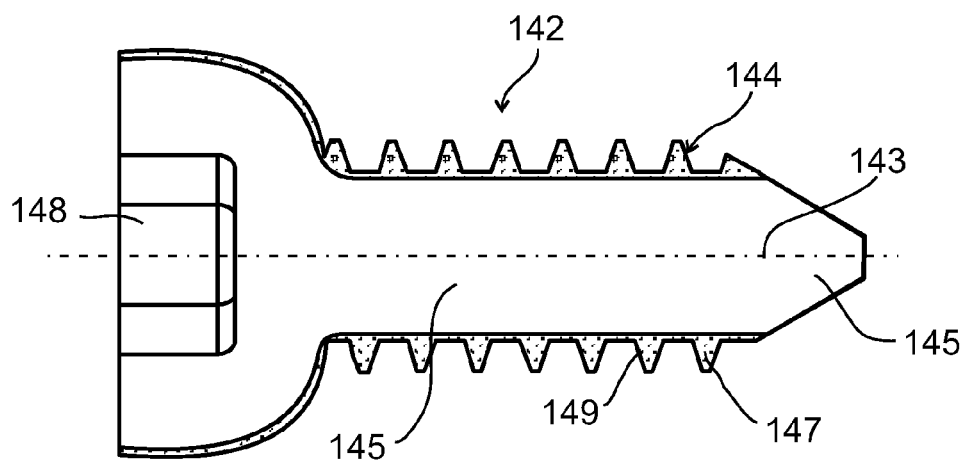
FIG. 12A
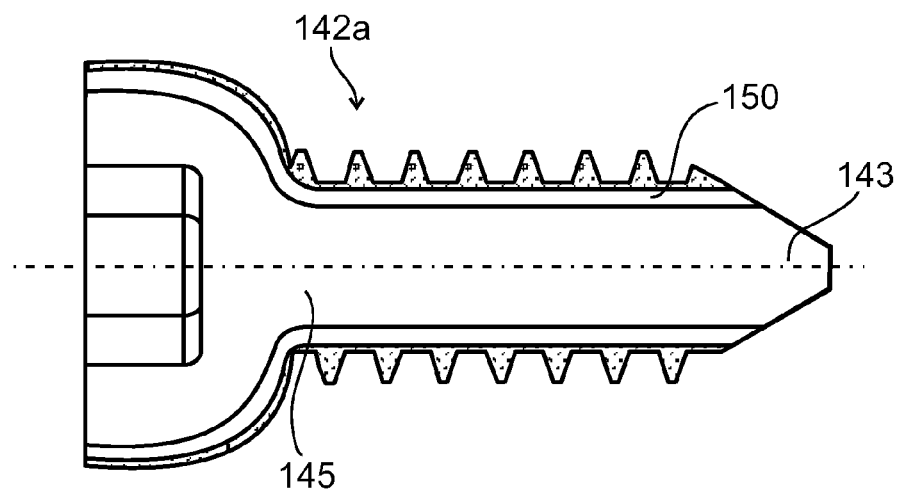
FIG. 12B

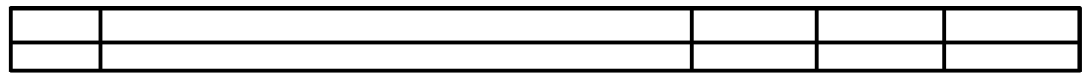
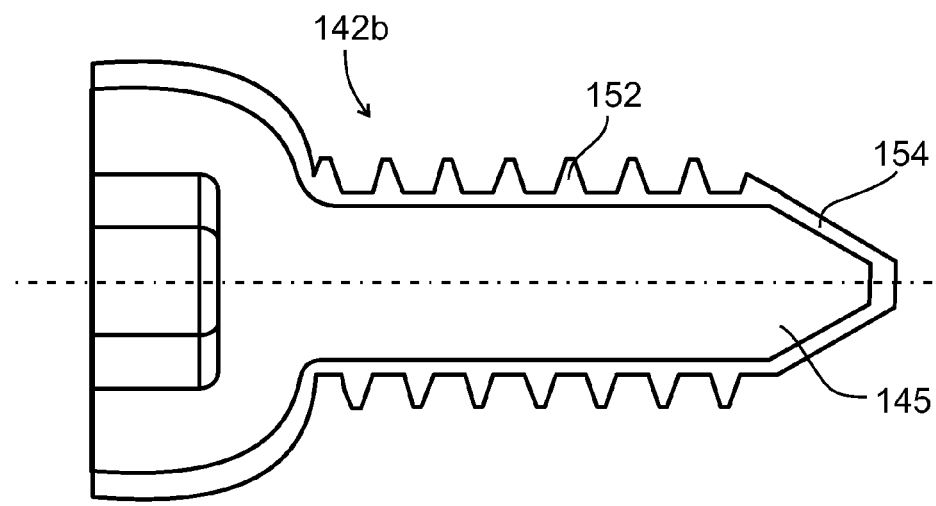
FIG. 12C
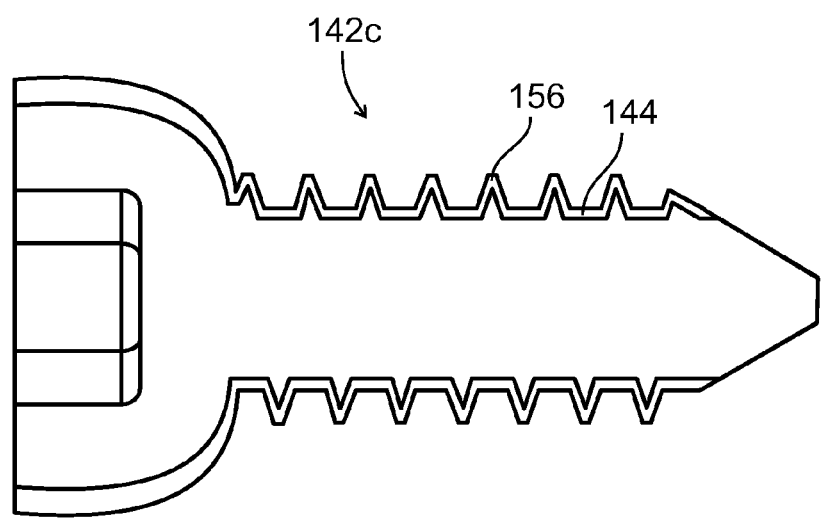
FIG. 12D

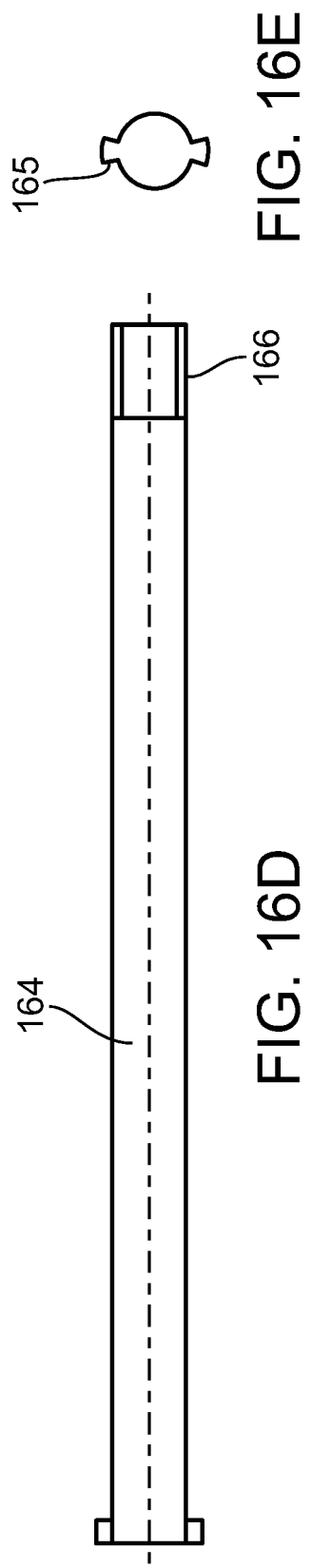

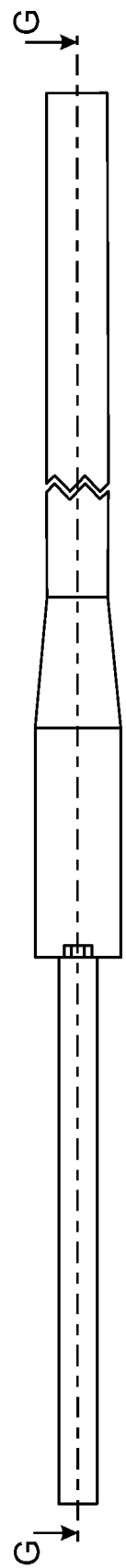
FIG. 16F
FIG. 16G

COMPOSITE MATERIAL BONE IMPLANT

RELATED APPLICATIONS

This application is a division of U.S. patent application Ser. No. 13/144,938 filed on Jul. 18, 2011, which is a National Phase of PCT Patent Application No. PCT/IB2010/050225 having International filing date of Jan. 18, 2010, which claims the benefit of priority of U.S. Provisional Patent Application Nos. 61/213,991 filed on Aug. 6, 2009 and 61/205,160 filed on Jan. 16, 2009. The contents of the above applications are all incorporated herein by reference.

FIELD OF INVENTION

The present invention in some embodiments thereof, relates to composite material bone implant devices and to manufacturing methods for such devices.

As used herein, the terms "bone implant devices" and "bone implants" are intended to encompass hip joints, knee joints, shoulder joints, bone screws, bone instruments, bone plates, and intramedullary nails, including proximal femur nails, typically including screw holes for receiving bone fixation screws.

BACKGROUND OF THE INVENTION

Intramedullary nails (bone nails) have become a treatment of choice for the fixation of bone fractures, especially fractures of long bones (e.g., the humerus, tibia and femur). Typically, bone nails are rod-shaped devices configured and constructed to be secured (interlocked) to a bone using one or more locking elements, such as transverse screws at one or both ends of the nail.

In many cases, the implant is constructed from metal, such as titanium, stainless steel or cobalt chromium. Although metallic implants provide numerous advantages, they also have a few drawbacks. Metal construction normally provides adequate bending strength, thus reducing problems associated with implant fracture and fatigue. However, the rigid metal implant creates a relative high degree of stresses in certain regions of the bone, while, on the other hand, does not provide for sufficient load transfer resulting in stress shielding. Both high stress and stress shielding can cause bone deterioration and resorption, leading to areas of bone weakness and loss of bone support for the implant (e.g., intramedullary nails and stem components of joint replacement systems). In addition, metals may result in artifacts in CT and MR imaging. Furthermore, metals such as stainless steel and cobalt chromium may cause biocompatibility problems related to corrosion and sensitization reaction (mainly due to allergy to nickel).

Non-metal implants made of a lighter and more flexible material, yet having sufficient strength for load bearing, have been suggested in the past. In particular, composite material implants, for example formed of polymer reinforced with fibers, are discussed in U.S. Pat. Nos. 4,750,905, 5,181,930, 5,397,358, 5,009,664, 5,064,439, 4,978,360, 7,419,714 the disclosures of which are incorporated herein by reference.

U.S. Pat. No. 5,009,664 describes a tubular, curved marrow nail, made of carbon fibers, which are preferably knit in a crisscross fashion, saturated in a hardenable plastic, with a conically tapered distal tip.

U.S. Pat. No. 5,181,930 describes an implant comprising an elongated core formed of continuous filament fibers embedded in thermoplastic polymer. The core is encased within a filler, made of a non-reinforced polymer which is molded around the core to proximate the final desired shape of the implant. A sheath, composed of reinforced fibers embedded in a polymer, is spiral wound around the filler, at angles (orientations) which may vary along the implant axis.

Although composite material implants can provide several advantages, they also have a few limitations. In contrast to metal, composite material implants are not visible under imaging devices (such as fluoroscopy), and hence their implantation as well as tracking during follow-up are difficult. U.S. Pat. No. 7,419,714 describes a bone screw or plate formed of a composite of polymer or ceramic material with reinforcing fibers, in which at least part of which are made of an X-ray absorbent material. For bone nails or plates, accurate insertion of the screws into the holes in the nail/plate is crucial to the success of the operation, especially where no aiming device is used. The use of interlocking screws poses a problem in such implants, as the designated holes at the nail ends (or at the plate), through which the screws are to be introduced, are not visible under fluoroscopy. The addition of fibers made of material that absorbs X-rays may be insufficient; as such fibers often do not adequately and accurately mark the hole. Also, in order to improve the visualization of implant hole a large quantity of such fibers might be required. In addition, with regards to intramedullary nails (or other implant construction that may comprise a weakened area), due to the composite material construction, the extremities of the nails at the area of the interlocking screw holes are more prone to damage.

Further, although such composite materials may have several properties that are claimed to be similar to those of bone, the composite material construction may be less efficient under torsion loads.

Additionally, the instrumentation that is used with a metal implant, such as an insertion handle, is usually connected to the implant via a thread at a proximal end of the implant. However, the composite material construction (which is not isotropic as is metal), has less resistance to shear forces, and damage (e.g., breakage) may result at the thread area.

The present invention addresses improvements in the above-noted areas, and in other areas of composite bone implant technology.

SUMMARY OF THE INVENTION

There is provided in accordance with an exemplary embodiment of the invention, a bone implant comprising:
a fiber reinforced polymer matrix body;
a passage through the body, open at opposite ends, and configured to receive a bone fixation screw; and
a radiopaque marking for location and orientation of the passage. Optionally, the passage is near a distal end of the body. Optionally or alternatively, the marking is comprised of at least one peripheral band of radiopaque material located inside the passage. Optionally or alternatively, the radiopaque marking is comprised of a plurality of localized areas of radiopaque material around the outside of the passage. Optionally, the radiopaque material is in the form of two rods located at each end of the passage.

In an exemplary embodiment of the invention, the radiopaque marking comprises a metal element extending along a longitudinal axis of the body.

In an exemplary embodiment of the invention, the implant is a bone plate, and the marking comprises at least one thin metal wire extending in a plane which is not subject to substantial bending strain.

In an exemplary embodiment of the invention, the implant is cannulated and the radiopaque marking is a thin metal layer extending along an inner surface of a lumen running through the implant body.

In an exemplary embodiment of the invention, the radiopaque marking is present in a quantity and configuration which results in levels of artifacts upon CT or MRI which do not significantly interfere with visualization.

In an exemplary embodiment of the invention, the localized areas are diametrically opposed, and are equally spaced from a longitudinal axis the respective passages, whereby correct orientation for insertion of the fixation screw into the passage is indicated when the rods at each end of a passage appear as single dots under fluoroscopic imaging.

In an exemplary embodiment of the invention a composite implant, optionally such as described above, is provided with a guide channel for a guide wire. Optionally such a channel is formed of a metal tube.

There is provided in accordance with an exemplary embodiment of the invention, a bone implant comprising:
 a fiber reinforced polymer matrix composite body;
 a connector at a proximal end of the body configured to be attached to an implant insertion tool in a single orientation, and adapted for bearing torsion applied by the insertion tool.

In an exemplary embodiment of the invention, a kit is provided including a bone implant as described above and an insertion tool including a connector interface having an alignment element adapted to engage with a complementary element of the connector in the single orientation. Optionally, the connector includes an internally threaded recess. Optionally or alternatively, a proximal end face of the connector includes a plurality of radial slots at extending inwardly from a periphery at the proximal end. Optionally or alternatively, the connector has a hexagonal configuration.

In an exemplary embodiment of the invention, the connector includes a bayonet configuration.

In an exemplary embodiment of the invention, the connector includes a metal insert configured to receive an implant tool.

There is provided in accordance with an exemplary embodiment of the invention, an end cap for a bone implant wherein the implant comprises a fiber reinforced polymer body and a connector at a proximal end of the body for receiving an insertion tool; wherein the end cap is configured to cover the connector when the implant is in place to inhibit tissue growth from preventing access to the connector for subsequent implant removal. Optionally, the connector is an internal recess and the end cap is externally configured to fit in the recess. Optionally or alternatively, the end cap includes a radiopaque marking. Optionally or alternatively, the end cap is formed of the same material as the implant body.

There is provided in accordance with an exemplary embodiment of the invention, a bone implant comprising:
 a body formed of a reinforced polymer matrix, and
 a passage through the body configured to receive a bone fixation screw, wherein the passage is configured to resist axial withdrawal of a bone fixation screw received therein. Optionally, the passage is a circular hole having a diameter that is smaller than an outside diameter of the screw. Optionally or alternatively, the implant comprises an elongated longitudinal slot at a proximal end of the body configured to slidably receive a bone screw therein, and to resist axial withdrawal of a received bone screw.

Optionally or alternatively, the resistance to axial withdrawal is provided by a ridge in an internal surface the circular hole and/or the slot. Optionally or alternatively, the passages are unthreaded.

There is provided in accordance with an exemplary embodiment of the invention, a bone implant comprising:
 a body formed of a reinforced polymer matrix; and
 a metal element incorporated in the body. Optionally, the metal element is an insert at a proximal end of the body configured to receive an implant insertion tool. Optionally or alternatively, the metal element is a smooth metal coating on the implant body.

In an exemplary embodiment of the invention, the insert is a coupling element. Optionally or alternatively, the insert is a structural element.

There is provided in accordance with an exemplary embodiment of the invention, a bone implant comprising:
 a body having a core constructed and configured to resist mainly bending forces; and
 a portion enclosing the core constructed and configured to resist mainly torsional forces;
 wherein the core and the surrounding portion are comprised of substantially linearly extending comingled long carbon and polymer filaments in a polymer matrix, and
 wherein at least part of the exterior surface is covered with a layer of metal. Optionally or alternatively, the enclosing portion is braided.

In an exemplary embodiment of the invention, the implant is in the form of an intramedullary nail, and enclosing portion is comprised of two layers of filaments helically wound in opposite directions. Optionally, the implant includes an outer layer comprised of linearly extending filaments.

In an exemplary embodiment of the invention, a proximal end is comprised of:
 a core of linearly extending filaments;
 at least two layers of filaments helically wound in opposite directions; and an outer layer comprised of filaments in a circular spiral configuration. Optionally, the helically wound filaments lie at about ±45 degrees to a longitudinal axis of the nail. In an exemplary embodiment of the invention, the core includes a substantially central, axially extending lumen.

In an exemplary embodiment of the invention, the implant is in the form of a bone plate. Optionally, the plate further includes a body molded around a plurality of passages configured to receive bone fixation screws. Optionally, the plate includes a radiopaque marking incorporated into the body.

There is provided in accordance with an exemplary embodiment of the invention, a bone fixation screw comprising:
 a composite core formed of a threaded, reinforced polymer body; and
 a metal exterior surface on the core. Optionally, the metal exterior surface is a plating having a smooth surface which does not promote integration with surrounding bone tissue when the screw has been implanted. Optionally or alternatively, the metal surface is comprised of titanium or a titanium alloy. Optionally or alternatively, the metal surface is thin enough that it does not cause artifacts in CT or MRI images that would interfere significantly with visualization. Optionally or alternatively, the metal surface is threaded.

In an exemplary embodiment of the invention, the screw threads are oversized or mismatched in pitch relative to screw holes in a bone implant configured to receive the screws. Optionally or alternatively, a portion of the composite core penetrates an inner surface of the metal threads.

In an exemplary embodiment of the invention, an interface between the composite core and the metal surface includes complementary projections and recesses.

In an exemplary embodiment of the invention, the material comprising the metal surface is crimped around proximal and/or distal ends of the composite core of the screw.

There is provided in accordance with an exemplary embodiment of the invention, a proximal femur (PF) nail assembly comprising:

an elongated stem having a proximal end; and a passage through the proximal end of the nail oriented at an angle to a longitudinal axis of the nail, the passage being oriented for anchoring the nail in the neck and head of the femur; and a bone fixation screw received in the passage, wherein the nail is a composite comprised of a reinforced polymer matrix. Optionally, the assembly includes a further passage is configured to receive an anti-rotation pin, wherein the anti-rotation pin passage extends parallel to the proximal end fixation screw passage. Optionally or alternatively, the screw is comprised of the same composite material as the nail, and includes a threaded metal shell.

In an exemplary embodiment of the invention, the assembly includes:

an insertion tool connector at the proximal end comprising an axially extending bore; and a cover configured to be received in the bore after the implant is in place to prevent bone or other tissue regrowth in the bore.

In an exemplary embodiment of the invention, the assembly includes a passage at a distal end of the body configured to receive a bone fixation screw; and a radiopaque marking for the location of the distal passage.

In an exemplary embodiment of the invention, the anti-rotation pin is metal.

In an exemplary embodiment of the invention, the passage for the proximal end fixation screw includes a holder for the screw.

There is provided in accordance with an exemplary embodiment of the invention, a tool for removing a bone implant, wherein the implant includes a body having an axial opening at a proximal end that communicates with a transverse passage, the tool comprising:

first and second arms;

a first transverse tip at a distal end of the first arm;

a second transverse tip at a distal end of the second arm extending in an opposite direction from that of the first tip; and a handle mechanism operable to move the first and second tips between a retracted position in which the tips are close to each other and an extended position in which the tips are separated, wherein the tips are sized and configured such that, in the retracted position, the tool is insertable into the axial opening in the implant, and in the extended position, the tips are within opposite sides of the screw passage, whereby axial force can be applied to withdraw the implant from inside an opening in a bone. Optionally, the first and second arms are crossed, and are connected at a pivot located between distal and proximal ends of the arms.

There is provided in accordance with an exemplary embodiment of the invention, a bone implant drilling assembly comprising:

a power unit; and a flexible cable connected between the power unit and a drill bit to transfer torque from the power unit to the drill bit. Optionally, the flexible cable is contained in an angled housing; and including:

couplings at opposite ends of the cable for attachment to the power unit and the drill bit. Optionally or alternatively, the power unit contained within the housing. Optionally or alternatively, the assembly is constructed for disposal after a single use. There is provided in accordance with an exemplary embodiment of the invention, a method of forming a bone plate comprised of a fiber reinforced thermoplastic polymer composite comprising:

pre-forming a bone plate based on average anatomical data;

obtaining specific anatomical data concerning an actual implant site for a particular patient;

heating the pre-formed bone plate and applying force to bend the pre-formed bone plate to the required shape; and cooling the bent bone plate in a manner which allows it to retain its bent shape without substantial change in its other properties. Optionally, the specific anatomical data is obtained by direct measurement of a patient's implant site during a surgical procedure. Optionally, the specific anatomical data is obtained radiologically or by an MRI or CT of a patient's implant site.

There is provided in accordance with an exemplary embodiment of the invention, a method of forming a bone nail comprised of a fiber reinforced thermoplastic polymer composite body and including a bend to conform to a particular implant site comprising:

pre-forming the bone nail without a bend;

heating the pre-formed bone nail while applying force to bend the pre-formed bone plate to the required shape; and cooling the bent bone nail in a manner which allows it to retain its bent shape without substantial change in its other properties.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE FIGURES

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a side elevation of bone implant in accordance with some embodiments of the present invention;

FIG. 2A is a cross-sectional view taken along line 2-2 in FIG. 1;

FIG. 2B is a pictorial illustration of an end cap for the proximal end of an implant according to some embodiments of the invention;

FIG. 3A is an enlarged fragmentary perspective view of the distal end of FIG. 2A showing a radiopaque marking for a screw hole according to some embodiments of the invention;

FIG. 3B is an enlarged fragmentary perspective view similar to FIG. 3A showing an alternative radiopaque marking for a screw hole according to some embodiments of the invention;

FIGS. 6A-6C are respectively schematic illustrations of a bone nail, a blowup a proximal end of the bone nail, and a blowup a distal end of the bone nail, according to some embodiments of the present invention;

FIG. 7 is a side elevation of a cannulated bone implant in accordance with some embodiments of the present invention;

FIG. 8 is a view rotated 90 degrees from FIG. 7;

FIG. 9A is a cross-sectional view taken along line 9-9 in FIG. 8;

FIG. 9B is an enlarged fragmentary view of the distal end of an implant as shown in FIGS. 8 and 9;

FIGS. 12A-12D are side elevations of bone fixation screws according to some exemplary embodiments of the invention;

FIGS. 16A-16G illustrate a bayonet coupling for the connection between the implant and an insertion tool, according to some embodiments of the invention.

DETAILED DESCRIPTION OF SEVERAL EMBODIMENTS OF THE INVENTION

Figure 3C:
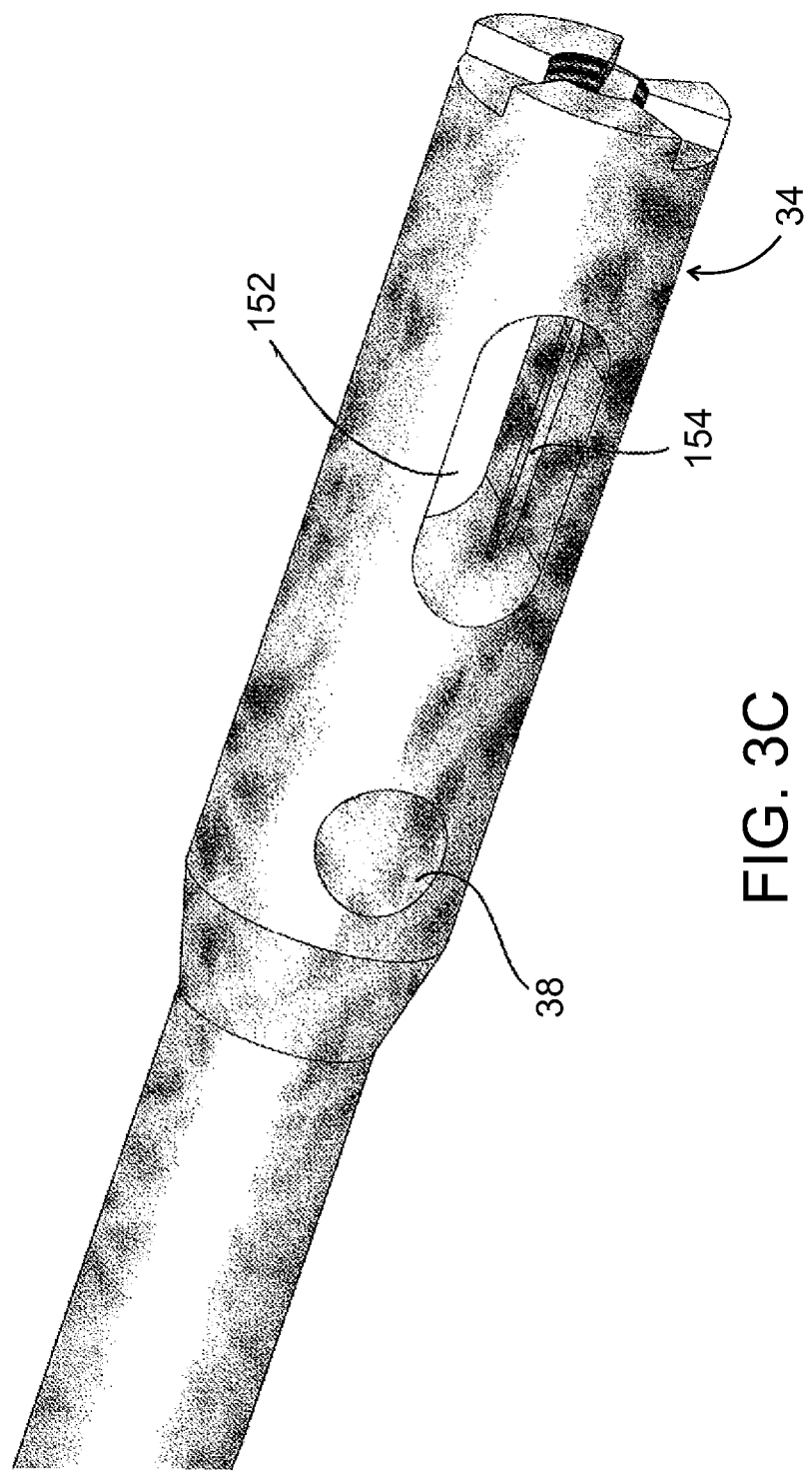
FIG. 3C is an enlarged perspective view of the proximal end of the implant of FIGS. 1 and 2A certain details of the internal construction of a screw hole and an elongated slot according to some embodiments of the invention.

The present invention, in some embodiments thereof, relates to composite material bone implant devices and to manufacturing methods for such devices. More particularly, but not exclusively, the invention relates to such devices and methods as applied to implant devices formed of fiber-reinforced polymer matrices or self-reinforcing polymers.

According to an aspect of some embodiments of the invention, implants are formed of a matrix of polymer material such as polyarylether ketone (PAEK), polyether ether ketone (PEEK), or other polyketone based polymers. Implants according to some embodiments of the invention may also be formed of a matrix polymer material such as but not limited to polyphenylene, polyphenylsulfone, or polysulfone. In all such embodiments, reinforcing fibers may included in the matrix. Optionally, these may be formed of carbon, ultrahigh density polyethylene (UHDPE), aramid polymers, or ceramic fibers such as glass. Optionally, two or more of these may be used together.

According to an aspect of some embodiments of the invention, the implant can be manufactured of a composite matrix material such as polyphenylene or UHDPE.

According to an aspect of some embodiments of the invention, in a bone implant having passages for receiving bone fixation screws, radiopaque marking visible under fluoroscopy is provided to show the locations of the passages. Optionally, the marking is in the form of at least one peripheral band of radiopaque material located inside each passage. In some exemplary embodiments, there are two spaced bands. In other exemplary embodiments, there is a single long band. Optionally, the long band extends substantially the length of the passage.

According to an aspect of some embodiments of the invention, the marking is in the form of a plurality of localized areas of radiopaque material around the outside of each passage. In some exemplary embodiments, two rods or pins are located at each end of each passage running parallel to the passage. Optionally, the rods are short compared to the length of the passage. Optionally, the rods are diametrically located, and are equally spaced from a longitudinal axis of the respective passages, whereby correct orientation for insertion of the fixation screw into the passage is indicated when the rods at each end of a passage appear as single dots when, for example, the X-ray beam is parallel to the passage.

According to an aspect of some embodiments of the invention, the implant is a bone nail, and a radiopaque marking is formed by at least one metal wire extending along a longitudinal axis of the body, in addition to or instead of the marking described above. The wire is interrupted by the fixation screw passages, so that the locations of the passages are indicated by the interruptions.

According to an aspect of some embodiments of the invention, the implant is a bone plate, and the radiopaque marking is formed by at least one metal wire extending in a plane which is subject to minimal changes in length during use due to substantial bending. The wire may be interrupted by the fixation screw passages, so that the locations of the passages are indicated by the interruptions.

According to an aspect of some embodiments of the invention, the implant is a cannulated bone nail and the radiopaque marking is a thin metal layer extending along an inner surface of a lumen running through the implant body. The metal layer is interrupted where the fixation screw passages cut through the lumen, so that the locations of the passages are indicated by the interruptions.

According to an aspect of some embodiments of the invention, the radiopaque marking is radiopaque filler, optionally barium, barium sulfate, zircona, etc. which can be pre-filled into the polymer matrix material in various concentration from 1-2 up to 40% by volume or mass, and incorporated in the implant. The filler is interrupted by the fixation screw passages, so that the longitudinal locations of the passages are indicated by the interruptions.

According to an aspect of some embodiments of the invention, to add hardness and strength to the implant, a metal or ceramic element is also embedded in the polymer implant. In some exemplary embodiments of the invention, the element is a nut embedded into the implant during manufacturing of the implant.

Alternatively, or additionally, in some exemplary embodiments of the invention, a metal layer may be applied to the surface of the implant, for example, as plating. The coating is made as smooth as possible to discourage integration with the surrounding bone tissue.

Optionally, the embedded elements and the coating are formed of titanium, titanium alloy or tantalum. Optionally, other suitable metals or metal alloys may be used.

According to an aspect of some embodiments of the invention, fixation screws, for example, for an intramedullary nail or bone plate are formed of the same composite material as the nail or bone plate itself. Optionally or additionally, the threads of the fixation screws are plated with a thin coating of metal such as titanium, titanium alloy (for example, Ti6Al4V), tantalum, gold, or any other biocompatible metal or metal alloy to improve shear strength, and surface hardness. The metal plating is thick enough to provide the needed additional strength, but thin enough that it does not cause an unacceptable level of CT or MRI image artifacts. In case artifacts are caused, they are sharply decreased compared to similar implants made of metals. The metal coating is made as smooth as possible to prevent attachment of re-grown tissue or bone to the threads, or the screw body, which would hinder removal of the screw if the implant must later be removed.

Normally, the bone fixation screws are threaded into the bone to anchor an implant such as a bone nail or plate. However, it is sometimes desirable or necessary, for example, in the case of osteoporotic bones which are soft, to lock the screw also into the implant to prevent axial withdrawal. According to an aspect of some embodiments of the invention, at lest some of the screw holes are slightly smaller than the outside diameter of the screw, or conversely, the outside diameter of the screws is slightly larger than the screw holes. Optionally, the screw holes may be threaded or unthreaded.

When the screw holes are unthreaded, during insertion, the screw pushes the implant material aside, or cuts its own thread, and locks into the surrounding material. In embodiments having threaded screw holes, the threads of the holes and the screws lock together due to the dimensional disparity.

Alternatively, the thread pitch for the screws and holes may be different. In such a case, the screw locks into the hole due to the pitch disparity.

According to an aspect of some embodiments of the invention, when there is a need for the screw to lock into the implant, at least some of the screw holes include a circumferential ring or ridge that reduces the diameter of the hole in a localized area. When the screw is inserted, it deforms the material of the ridge or cuts a thread allowing it to lock into the implant.

It should also be noted that according to some embodiments of the invention, bone screws as described herein may be used as standalone implements to attach two parts of broken bone, without a nail or plate.

According to an aspect of some embodiments of the invention, a bone nail is formed with a longitudinal slot at its proximal end. After the nail has been attached to the broken bone at its distal end by a bone screw, and the broken parts of the bone have been aligned, the surgeon can apply compression to the fracture site by attaching a screw to the bone through the slot and pulling the nail against the screw in the slot, optionally using the implant insertion tool. One or more other screws at the proximal end may be added to anchor the nail.

According to an aspect of some embodiments of the invention, the slot may include a ridge or rib to prevent withdrawal of the screw from the slot, as in the case of the round screw hole described above.

According to an aspect of some embodiments of the invention, a bone nail implant includes a connector, optionally an internally threaded recess at its proximal end, for attachment of an insertion tool having complementary external threads. Optionally, the recess is configured with a plurality of radial slots on its end surface. Alternatively, the end may have a hexagonal external configuration capable of bearing torsion.

Optionally, the connection configuration permits only a single manner of connection, thus assuring connection in the proper orientation According to an aspect of some embodiments of the invention, a closure cap is provided for the open end of the connector, optionally formed of the same material as the implant body, optionally without the fibers, and includes external threads which engage the internal threads of the connector. Closing the connector serves to inhibit tissue growth in the open connector end that could hinder access to the connector by a removal tool for subsequent implant removal if necessary.

Optionally, a closure cap as described includes radiopaque marking.

Optionally, according to some exemplary embodiments of the invention, the nail may be cannulated. For such a construction, the core includes a substantially central, axially extending lumen. Optionally, according to some embodiments of the invention, the inner surface of the lumen has a metal coating which serves as a marking.

According to an aspect of some embodiments of the present invention, an intramedullary nail is formed with a core constructed and configured to resist mainly bending forces (for example, about 75% or more of the forces encountered are bending forces), and a sleeve enclosing the core, for resisting mainly torsional forces (for example, about 75% or more of the forces encountered are torsional forces). In some exemplary embodiments, the core and an outer layer are formed of substantially linearly extending comingled long carbon and polymer filaments in a polymer matrix. The sleeve is intermediate the core and the outer layer. According to some embodiments, the sleeve is braided, i.e., it is formed of two oppositely wound helical layers, for example, at ±45 degrees. Optionally, the exterior is coated with a layer of metal such as titanium, titanium alloy or tantalum.

According to some embodiments of the invention, at the proximal end, the fibers in one or more layers are oriented helically with very small pitch, or optionally, circularly, around the main axis of the nail. That orientation increases the strength of the engagement of the nail and the insertion tool.

Optionally, if the implant is likely to experience high local stresses at the installation site, or during insertion or removal, an insert may be provided, optionally in the form of metal nut.

Alternatively, or additionally, the surface of the implant may be provided with a metal coating. The net, the metal insert, and the coating are optionally formed of titanium or titanium alloy, or any other suitable and desired metal or metal alloy.

According to an aspect of some embodiments of the present invention, a bone plate has a woven or braided body formed of substantially linearly extending comingled long carbon and polymer filaments in a polymer matrix.

Optionally, passages for receiving bone fixation screws are formed in the molding process when the plate is fabricated. Optionally, the passages are formed, for example, by machining, after the plate has been fabricated.

According to an aspect of some embodiments of the present invention, a bone plate is preformed of a reinforced thermoplastic polymer, based on average anatomical data, and then bent to a final shape before implantation based on specific anatomical data concerning the actual implant site for a particular patient. According to some exemplary embodiments, the final shaping is done by heating the pre-formed implant and applying force to bend it to the required shape, then cooling the bent implant in a manner which allows the implant to retain its bent shape without substantial change in its other properties.

Optionally, the specific anatomical data is obtained by direct measurement of the patient's implant site during a surgical procedure, or even visually. Optionally, the specific anatomical data is obtained radiologically or by an MRI or CT of the patient's implant site.

According to an aspect of some embodiments of the invention, a bone fixation screw may be formed of the same fiber reinforced or self reinforcing polymer materials as the implant itself. Optionally, to provide added shear strength, the screw threads are coated with a thin layer metal, for example, titanium, titanium alloy, tantalum, gold, or any other biocompatible metal or metal alloy. The metal coating should be thick enough to provide the needed additional strength, but thin enough that it does not cause artifacts in CT images or MRIs.

According to an aspect of some embodiments of the present invention, a proximal femur (PF) nail includes an elongated stem having a proximal end and at least one passages through the proximal end oriented at an angle to a longitudinal axis of the nail to receive a proximal end bone fixation screw for anchoring the nail in the neck and head of the femur, wherein the nail is comprised of a reinforced polymer matrix. Optionally, the PF nail includes a further passage configured to receive an anti-rotation pin, which passage extends parallel to the proximal end fixation screw passage. Optionally according to some exemplary embodiments of the invention, a PF nail includes radiopaque markings for at least one passage.

Optionally according to some exemplary embodiments of the invention, a PF nail includes an insertion tool connector comprising an axially extending bore at a proximal end of the nail; and a cover configured to be received in the bore after the nail has been implanted to prevent tissue and bone regrowth in the bore.

Optionally, in a PF nail as described above, the reinforced polymer matrix includes at least one layer of reinforcing fibers extending longitudinally in the nail body.

Optionally, in a PF nail as described above, the passage for the proximal end fixation screw (also called a leg screw) is configured to receive a holder for the screw.

Optionally, the PF nail is long enough to treat femoral shaft fractures in addition to the proximal femur fractures.

According to an aspect of some embodiments of the invention, a bone implant includes a PF nail as described above, and a leg screw for anchoring the implant in the neck and head of the femur. Optionally, the leg screw is formed of the same material as the nail. Optionally, the screw is formed of metal, for example, a titanium alloy. Optionally, the implant includes an anti-rotation pin extending parallel to the leg screw.

According to an aspect of some embodiments of the invention, a bone screw for a PF nail as described above is formed of a core of the same material as the nail. Optionally, the screw includes a metal shell surrounding the reinforced polymer core. Optionally, the metal shell is threaded at a distal end. Optionally, a portion of the polymer core penetrates an inner surface of the metal threads. Optionally, an interface between the polymer core and the shell includes complementary projections and recesses. Optionally, the metal shell is crimped around proximal and/or distal ends of polymer core of the screw.

According to an aspect of some embodiments of the present invention, an implant removal tool is constructed to engage an installed implant through an axial opening at a proximal end of the implant that communicates with a transverse passage configured to receive a bone fixation screw.

According to some exemplary embodiments, the tool includes first and second arms, each having a transverse tip at its distal end, and a lever mechanism operable to move the first and second tips between a retracted position in which the tips are close to each other and an extended position in which the tips are separated.

According to some exemplary embodiments, the tips are sized and configured such that, in the retracted position, the tool is insertable into the axial opening in the implant, and in the extended position, the tips are within opposite sides of one of the screw passages, optionally the slot used to compress the fracture site, whereby axial force can be applied to withdraw the implant from inside an opening in a bone.

According to some exemplary embodiments, the first and second arms are crossed as in a pair of scissors, and are connected at a pivot located between distal and proximal ends of the arms.

According to some exemplary embodiments, the first and second arms are opposed but not crossed, and are connected at a pivot point located at proximal ends of the arms. Optionally, the pivot includes a spring which maintains the tips in the extended position when the spring is in an uncompressed state, and draws the tips to their retracted position when it is compressed.

According to an aspect of some embodiments of the present invention, a bone drill for drilling a bone to receive a bone implant includes a power unit and a substantially radiolucent angled connector configured to be fitted between the power unit and a drill bit, According to some exemplary embodiments, the connector includes an angled housing, couplings for attachment to a drill power unit and a drill bit, and a flexible cable. Optionally, the connector is constructed for disposal after a single use.

According to an aspect of some embodiments of the invention, the connection between the implant and an insertion tool is a bayonet coupling rather than threaded.

According to an aspect of some embodiments of the invention, a bone nail which will have a bend as part of its final shape is preformed without a bend, and then subjected to heat and a bending force in a mold. The bent nail is then cooled according to a protocol which allows it to retain its bent shape and other original properties.

DETAILED DESCRIPTION OF SOME EMBODIMENTS OF THE INVENTION

Before proceeding with the detailed description of the embodiments of the invention, it is noted that the devices and parts to be described are all formed of a matrix of Thermoplastic polymer material or thermoset polymeric resins. thermoplastic polymers such as polyarylether ketone (PAEK), polyether ether ketone (PEEK), other polyketone based polymers such as OXPEKK®, made by Oxford Performance Materials, Enfield, Conn., polyphenylene, polyphenylsulfone, polyamide-imide, polyphenylene sufide or polysulfone, or similar. thermoset polymeric resins such as epoxy, polyester, polyimide or bismaleimide Reinforcement may be provided by carbon and/or ultrahigh density polyethylene (UHDPE) fibers such as Spectra® from Honeywell, of Colonial Heights, Va., or Dyneema®, from DSM Dyneema of Heerlin, the Netherlands, aramid fibers, e.g., Kevlar®, from DuPont of Wilmington, Del., quartz, basalt, polyethylene, boron or glass. Optionally, two or more of these may be used together. Optionally, the fibers constitute 40 to 80 percent by volume of the implant material. In an exemplary embodiment, the fibers constitute 60 percent by volume of the implant material.

Alternatively, according to some embodiments of the invention, the implant can be manufactured of a self reinforcing composite material such as Dyneema.

Turning now to the drawings, FIGS. 1 and 2A respectively illustrate a side elevation and a cross-sectional view taken along line 2-2 in FIG. 1 of an intramedullary nail in accordance with some embodiments of the invention. The nail, generally denoted at 30 is comprised of an elongated body 32 formed of a fiber reinforced polymer matrix as described above.

Figure 4:
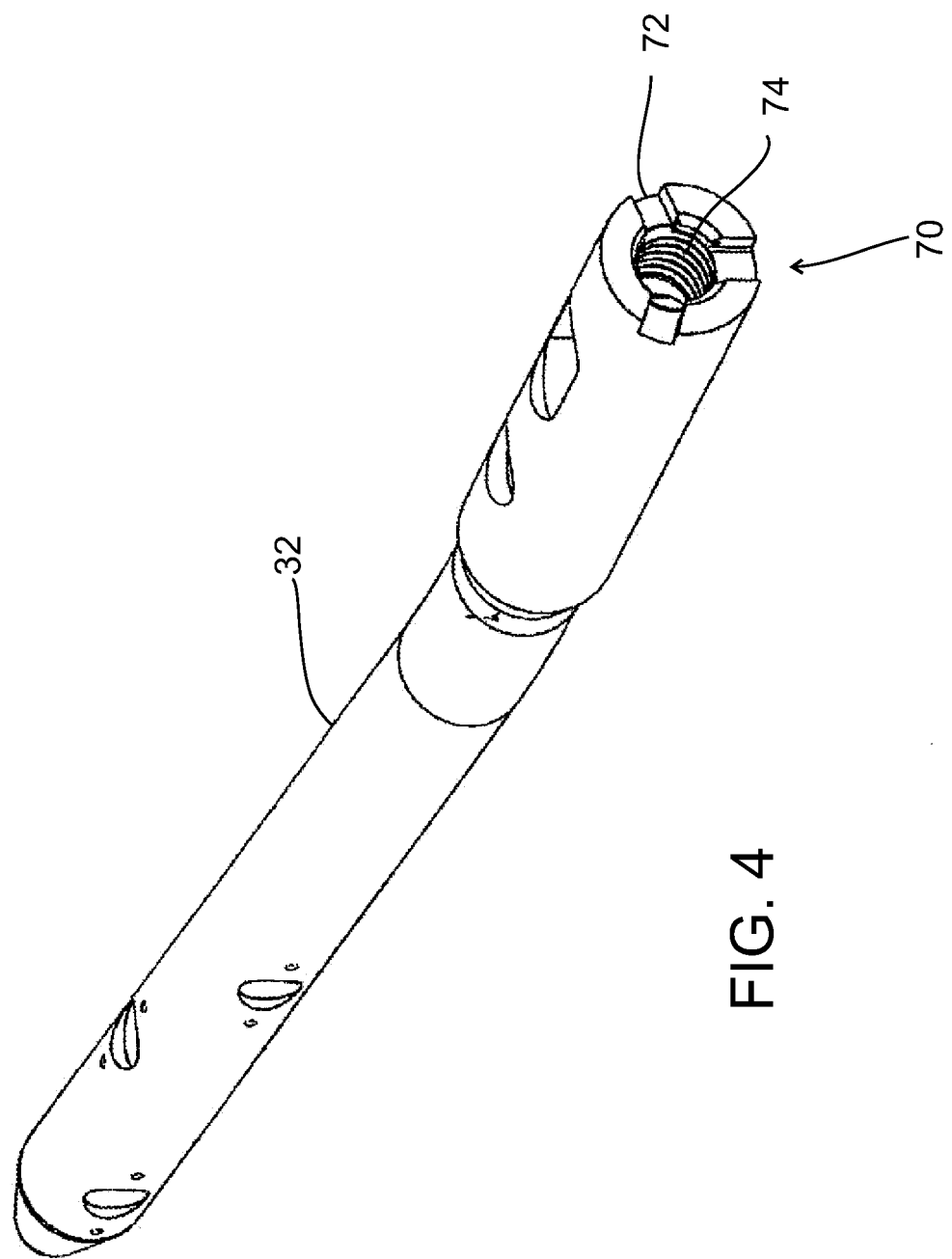
FIG. 4 is perspective view seen from the proximal end of a bone nail showing details of a connector for an insertion tool according to some embodiments of the invention.
Figure 5:
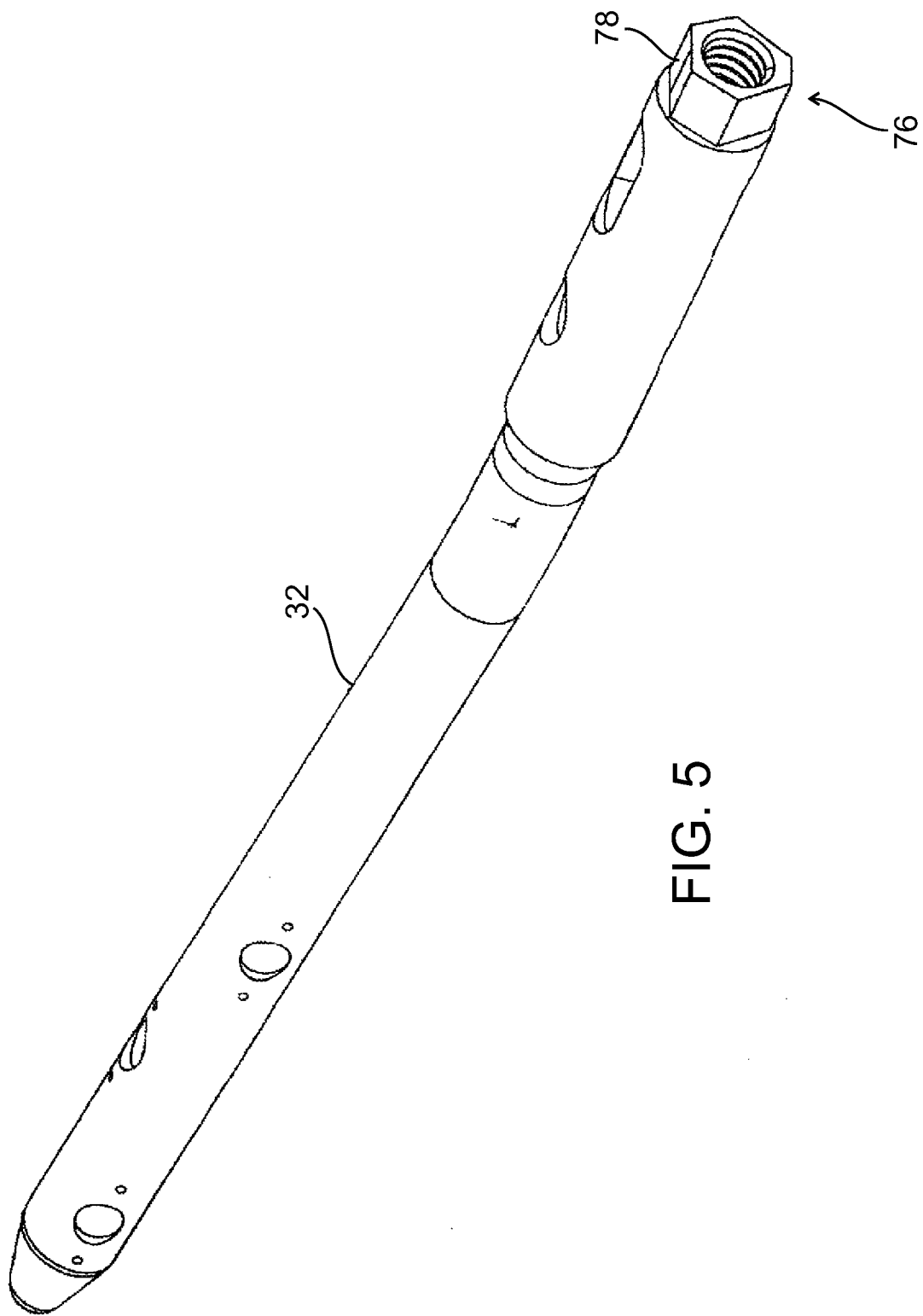
FIG. 5 is a perspective view similar to FIG. 4 showing a variation of the proximal end of a bone nail according to some embodiments of the invention.

At a proximal end 34, body 30 includes one or more generally round screw holes (one being shown by way of example at 38), extending through body 32, a longitudinally elongated slot 40, also extending through body 32, and an crown portion generally denoted at 42, As shown in FIGS. 4 and 5, proximal end 34 includes a threaded axial bore 44 extending into an connector portion 42, configured to engage an insertion tool as described below. Optionally, bore 44 extends axially a sufficient distance to communicate with the proximal end of slot 40 to facilitate axial compression of the nail to the bone prior to insertion of all the interlocking screws, and for connection of an implant removal tool, also as described below.

At a distal end 36, body 32 includes one or more generally round screw holes (one of which is indicated at 46) extending sidewardly through body 32, and optionally, one or more generally round screw holes 48 extending for example at a 90 degree angle to screw hole 46.

Optionally, some (or all) of the screw holes may be threaded, as indicated by hole 38, or unthreaded, as indicated by holes 46 and 48.

Implants as described above formed of fiber reinforced polymer, may be fabricated in any of several conventional ways, generally using heat and pressure such as compression molding, or injection molding. These are well known to persons of ordinary skill in the art, so further description is omitted in the interest of brevity. In the case of self reinforcing polymers such as Dyneema, the implant may be fabricated by the known technique of holding a bundle of thermoplastic fibers oriented in a desired direction, and rapidly heating and cooling the fiber bundle under pressure in a mold so the outer the fibers melt together to create the matrix, while the core fibers do not have time to melt, and thus keep their very high strength.

According to some embodiments of the invention, radiopaque markings are provided to assist the surgeon in locating screw holes 46 and 48, etc. and slot 40 for accurate insertion of bone fixation screws, not shown, but as described below. The markings may take various forms, as illustrated in FIGS. 1 and 2, FIGS. 3A through 3C, and also FIGS. 9A and 9B.

By way of example, screw hole 46 is marked by four short metal rods or pins 50, two at each end of hole 46, best illustrated in FIGS. 2A and 3A. Rods 50 extend parallel to screw hole 46 and are equally spaced diametrically from the center of the hole, As best seen in FIG. 3A, rods 50a and 50c are located at one end of screw hole 46, and rods 50b and 50d are located at the opposite end. Rods 50a and 50b are aligned on one side of screw hole 46, and rods 50c and 50d are aligned on the opposite side.

During the implant procedure, the implant site is visualized fluoroscopically. As will be understood, when hole 46 and markings 50 are viewed from the proper axial position for insertion of the fixation screws, rods 50a and 50b and 50c and 50d respectively appear as single dots equally spaced diametrically from the center of the hole (see FIG. 1). By inserting the screw at the center thus indicated, and with the rods appearing as single dots, proper positioning of the screw is achieved.

Another form of radiopaque marking is illustrated in FIG. 3A. Here, the markings comprise two thin metal rings 52a and 52b located inside a screw hole 54. Rings 52 may be formed by plating the surface of hole 54, or may be inserted into the hold and radially expanded or may be inserted into the body of the implant as part of the molding process, As will be appreciated by those skilled in the art, when screw hole 54 is visualized fluoroscopically from the proper axial orientation, the rings 52a and 52b appear as a single circular ring.

FIG. 3B illustrates a variation of the marking arrangement of FIG. 3A, in which a single metal tube 58 is provided extending substantially the entire length of the inside of a screw hole 56. As will be appreciated, when such a marking is viewed at the proper axial orientation for insertion of the fixation screw, it appears as an undistorted circle.

It should be noted that marking is needed mainly for screw holes at the distal part of the nail. For the proximal end, an external aiming device may be used that is attached to the proximal end of the nail during insertion, according to conventional practice.

Other forms of radiopaque markings for the screw holes, 46 and 48 are also possible. For example, body 32 may include one or more longitudinally extending wires, such as axial wire 59 (see FIG. 2). In the case of a bone plate, in some exemplary embodiments, the wire is optionally located in a plane which subject to minimum change of length due to bending.

In the case of a cannulated nail for use in long bones such as the femur and tibia, a marking may optionally take the form of a thin metal tube on the inside of an internal lumen (see description below). Another option is to include a quantity of radiopaque filler, for example, barium, in the polymer matrix.

It should be understood such alternatives, the screw holes cause discontinuities which indicate only longitudinal location, but not provide drilling direction information.

Suitable metals for use as markings include, tantalum, gold, or other biocompatible materials having high atomic numbers. In an exemplary embodiment, the metal is tantalum.

In all instances, it is to be understood that the size of the markings should be sufficient to be clearly visualized fluoroscopically, but not large enough to cause significant artifacts in CT images or MRI. In some exemplary embodiments, wires such as 59 may have a diameter in the range of 0.05-0.4 mm, for example, 0.2 mm. Rods 50 may have a diameter in the range of 0.2-1 mm, for example, 0.7 mm.

As previously mentioned, the proximal end of nail 30 comprises a connector including a threaded bore 44 for attachment of an implant insertion tool. Referring now to FIG. 2B, there is shown an end cap 60 configured to be threadedly received within threaded bore 44 upon completion of the nail implant procedure.

The purpose of end cap 60 is to provide a closure for bore 44 which prevents regrowth of bone or other tissue inside the bore which would hinder insertion of an implant removal tool should removal of the implant later be necessary. End cap 60 includes slots 62 at its end to facilitate its own insertion and removal, but other configurations are possible, as will be recognized by persons skilled in the art.

End cap 60 may optionally be formed of the same matrix material (for example PEEK) as body 32, without fibers, and may be fabricated in any conventional or desired manner. End cap material can include radiopaque marking, for example, spaced rods or pins 64.

Normally, an implant such as a bone nail or plate is attached to the underlying bone by the fixation screws (not shown) which are threaded into the bone through holes in the bone implant. However, in some instances, such as for osteoporotic bones that are soft, it may be desirable or even necessary to lock the screw also into the implant to prevent axial withdrawal. In some embodiments of the invention, this is accomplished by making at least some of the screw holes slightly smaller than the outside diameter of the screw, or conversely, by making the outside diameters of the screws slightly larger than the screw holes. Optionally, the screw holes may be threaded or unthreaded. When the screw holes are unthreaded, during insertion, the screw pushes the implant material aside, or cuts its own thread, and locks into the surrounding material. In embodiments having threaded screw holes, the thread pitch may be different on the holes and the screws so the two lock together due to the dimensional or pitch disparity.

Alternatively, to provide for locking the screw into the implant, at least some of the screw holes such as 38 at the proximal end of implant 30 may include a ridge or rib similar to rib 154 shown in FIG. 3C that reduces the diameter of the hole in a localized area. When the screw is inserted, it deforms the material of the rib, or cuts a thread allowing it to lock into the implant.

FIG. 3C illustrates an additional feature according to some embodiments of the invention. As shown, a bone nail is formed with a longitudinal slot 152, for example, at its proximal end 34. After the nail has been attached to the broken bone at its distal end, for example by a bone screw extending through hole 46 (see FIG. 2), and the broken parts of the bone have been aligned, the surgeon can apply compression to the fracture site by attaching a screw to the bone through slot 152 and pulling the nail against the screw in the slot, optionally using the implant insertion tool. One or more other screws at the proximal end may then be added, for example, through hole 38, to anchor the nail.

According to some embodiments of the invention, slot 152 may include a ridge or rib 154 to prevent withdrawal of the screw from the slot, as in the case of the round screw hole described above.

Referring now to FIGS. 4 and 5, there are shown alternative constructions for a connector for an implant insertion tool or handle. In one illustrative embodiment, a connector 70 shown in FIG. 4 includes a grouping of radial slots 72 (for example, three as illustrated), which are configured to engage a complementary end of a conventional implant insertion tool (not shown) in the required orientation, according to conventional implant insertion practice. Preferably, more than one slot 72 is employed; as composite materials generally provide limited shear strength relative to metal, and multiple slots help assure sharing of the shear load imposed by the torque applied by the insertion handle. Alternatively, more than three slots 72 may be employed, provided they are arranged at the proper orientation relative to the insertion handle.

In another illustrative embodiment shown in FIG. 5, connector 76 may have a single position at which it can connect to the insertion tool. Illustratively, this may be a generally hexagonal external configuration indicated at 78 capable of bearing torsion.

In the exemplary embodiments illustrated, connectors 70 and 76 are formed of the same reinforced polymer material as the rest of the implant body. Optionally, the connectors may be formed of a metal end attachment (for example, titanium or the like) or ceramics molded into the proximal end of the implant body, provided it does not interfere unacceptably with CT or MRI visualization.

According to some embodiments of the invention, bone implants as described in connection with FIGS. 1-5, are formed of fiber layers designed to resist mainly bending forces, and mainly torsional forces. (As previously mentioned, the term "mainly" is considered to mean that the forces encountered are at least about 75 percent bending forces or at least about 75 percent torsional forces.)

FIGS. 6A, 6B, and 6C show some details of a bone nail 89 according to such embodiments.

Here, core 90 and an outer layer 92 are formed of long substantially linearly extending fibers parallel to a longitudinal axis 94 within a polymer matrix.

In the embodiments of FIGS. 6A, 6B and 6C, the nail is cannulated for illustrative purposes. Optionally, an internal lumen 114 is covered with a metal layer 130, for example, a metal tube, optionally inserted during compression molding of the nail.

Alternatively, in some embodiments, the nail is non-cannulated. In such embodiments, the core may be solid, but may be otherwise the same as core 90 illustrated.

Referring to FIG. 6B, core 90, are multiple layers 100 of filaments in a polymer matrix helically wound in opposite directions, example, at ±45 degrees. Layers 100 are optionally wound or braided after manufacturing the longitudinal core 90. Optionally this may be formed by winding impregnated strips of composite material. One or more layers oriented in opposite direction are employed to resist the torque applied on the nail in the two directions of rotation. Optionally, at the proximal end 104, layer 100 is comprised of helically oriented filaments formed by winding multiple layers of impregnated strips of composite material in opposite directions, for example, at approximately +45 and −45 degrees.

It should be noted that some variability in the direction of the fibers is optional. For example, the windings 100 may be oriented at angles in the range of ±35 to 55 degrees.

Optionally, fibers may braided to combine two neighbor layers.

Optionally, the outer surface may be coated, at least partly, for example by plating, with a layer 110 of titanium, tantalum or similar metal.

Optionally metal outer surface 110 may be manufactured by compression molding the composite into a metal shell.

Referring to FIG. 6C, the distal end 106 may be of the same construction as the proximal end. Illustratively, however, it is shown without a metal layer, and with only two helical layers 112.

As an example of the construction illustrated in FIG. 6A, for an intramedullary nail having an outside diameter of 8.5 mm, the inner, linear fiber layer embedded within the polymer matrix may have a diameter of up to 7.6 mm. If the nail is cannulated, internal lumen diameter may be 2.7 mm, metal cover (if any) will be between diameters 2.7 to 2.9 mm. The second layer of helical fibers may have a thickness of 0.3 mm between diameter 7.6 mm and diameter 8.2 mm. The third (outer) layer of linearly extending fibers embedded in a polymer matrix may have a thickness of 0.15 mm between inner and outer diameters 8.2 mm and 8.5 mm.

As an example for cannulated nail having a proximal head with a final diameter of 11.6 mm, an inner lumen may have a 2.7 mm diameter, metal cover (if included) will be from 2.7 to 2.9 mm in diameter, linear fiber layer may have a diameters from 2.9 up to 7 mm. A first helical in −45 deg, orientation may be from 7 to 7.4 mm in diameter. A second layer of helical fibers in +45 deg, may be from 7.4 mm to 7.8 mm in diameter. One more helical layer in −45 deg. may be from 7.8 to 8.2 mm in diameter, one more helical layer in +45 deg may be from 8.2 to 8.6 mm in diameter, and helical circular layer may be between 8.6 and 10.8 mm in diameter. An outer layer of longitudinal fibers may be between 10.8 mm and 11.6 mm. in diameter.

Optionally, according to some exemplary embodiments, and as shown in FIGS. 6A-9B, a nail 107 may be cannulated. One optional use for a cannulated nail is repair of long bones such as the femur, tibia and humerus. As illustrated, in FIGS. 7-9B, nail 107 includes an elongated body 109 having a proximal end 110, a distal end 113, and a substantially central, axially extending lumen 114.

Distal end 113 includes a longitudinal slot 116 and a round hole 118 extending in the same direction through the nail, and round holes 120a and 120b extending at a 90 degree angle to slot 116 and hole 118. Proximal end 110 includes round screw holes 122 and 124, and a slot 126.

Each of the screw holes and slots at distal end 113 and proximal end 110 of nail 107 may include radiopaque location markings. As seen in FIG. 9B, these may take the form of rods or pins 128 as described in connection with FIGS. 2A and 3C, or rings as described in connection with FIGS. 3A and 3B. Additionally, or alternatively, a thin metal tube 130 may be bonded in any suitable manner on the inner surface of lumen 114 (the distal end of which is best seen in FIG. 9B).

As in the case of the embodiments employing wire 59 shown in FIG. 2, or employing the radiopaque filler in the matrix, the continuity of tube 130 is interrupted by the screw holes and the slots, so that the longitudinal positions of these passages is indicated under fluoroscopy by the resulting discontinuities. As will be appreciated, tube 130 also serves to mark the location and extent of implant 107 itself.

Cannulated implant 107 is otherwise the same as that previously described in connection with FIGS. 1, 2, and may include a connector at its proximal end 110 like that described in connection with FIGS. 4 and 5, and an end cap as described in connection with FIG. 2B. Also, it may be formed with the same layer configuration as in FIG. 6A. Accordingly, further description is omitted in the interest of brevity.

Optionally, implants according to some embodiments of the invention may include additional elements to improve performance, mainly strength. For example, an insert can be made of metal or ceramics, or isotropic composite parts. One such embodiment is illustrated by way of example, in FIGS. 10A-10C.

Figure 10A:
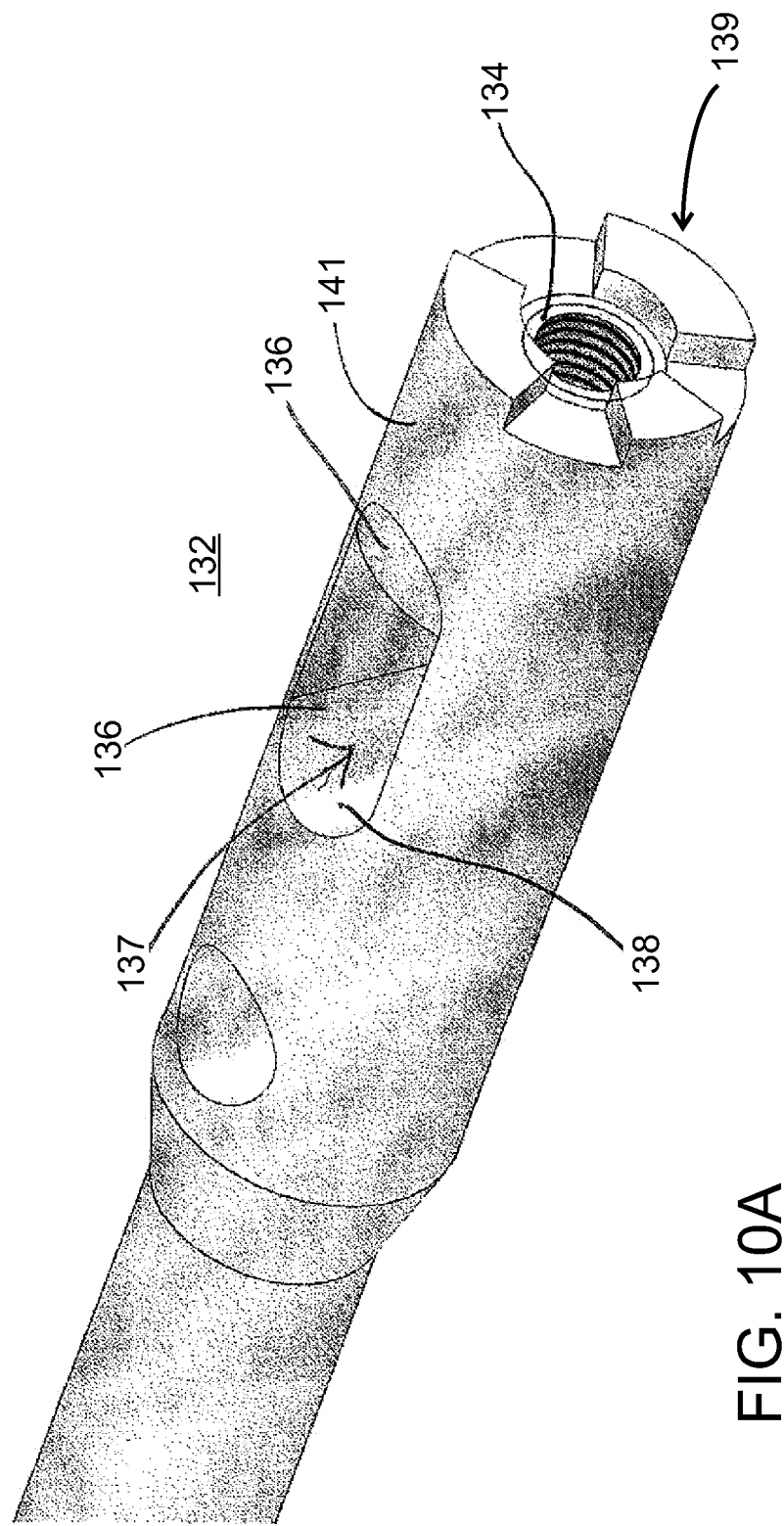
FIG. 10A is an intramedullary nail including a metal nut to impart added strength to the connection between the implant, according to some embodiments of the present invention.

In FIG. 10A, there is shown an intramedullary nail 132 including a metal nut 134 to impart added strength to the connection between the implant, and the insertion handle. This may be embedded optionally into the implant during molding. Optionally, the nut 134 may by inserted into the proximal slot, and pushed into the proximal side of the nail.

Figure 10C:
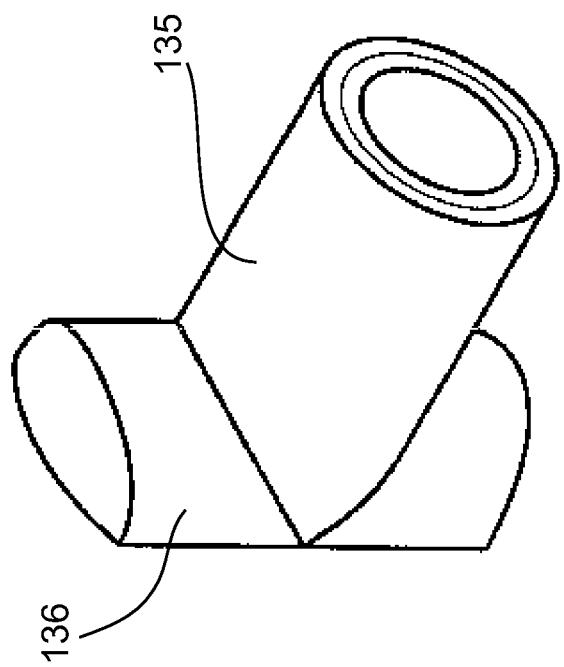
FIGS. 10B and 10C are illustrations of T shaped nuts according to some embodiments of the invention.
Figure 10B:
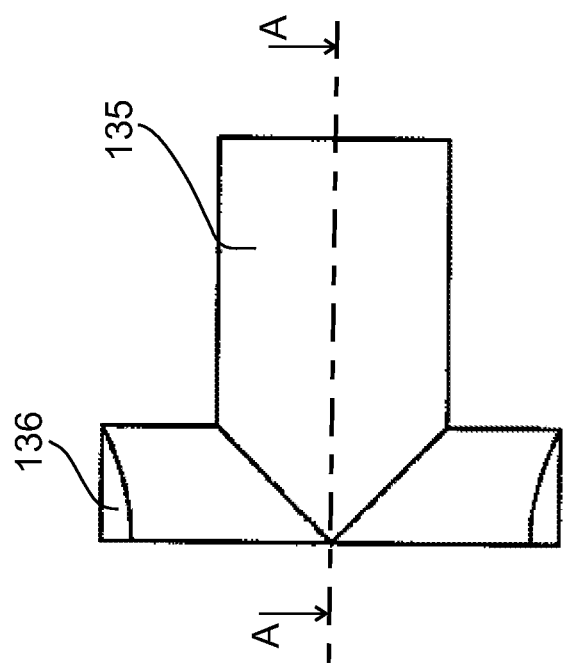

In FIGS. 10B and 10C there are illustrated one option of the nut insert 134. As shown, nut 134 is generally T-shaped with a body 135 and opposed arms 136. When not molded in, nut 134 is oriented as shown in FIGS. 10B and 10C, and placed in slot 137 near its distal end 138. It is then moved in the proximal direction so that body is within the axial bore at the proximal end 139 of the implant.

Alternatively, or additionally, the surface of the implant may be provided with a metal coating or plating 141. The metal insert and the coating may be formed of titanium, titanium alloy or tantalum, or any other suitable and desired metal or metal alloy.

Figure 11:
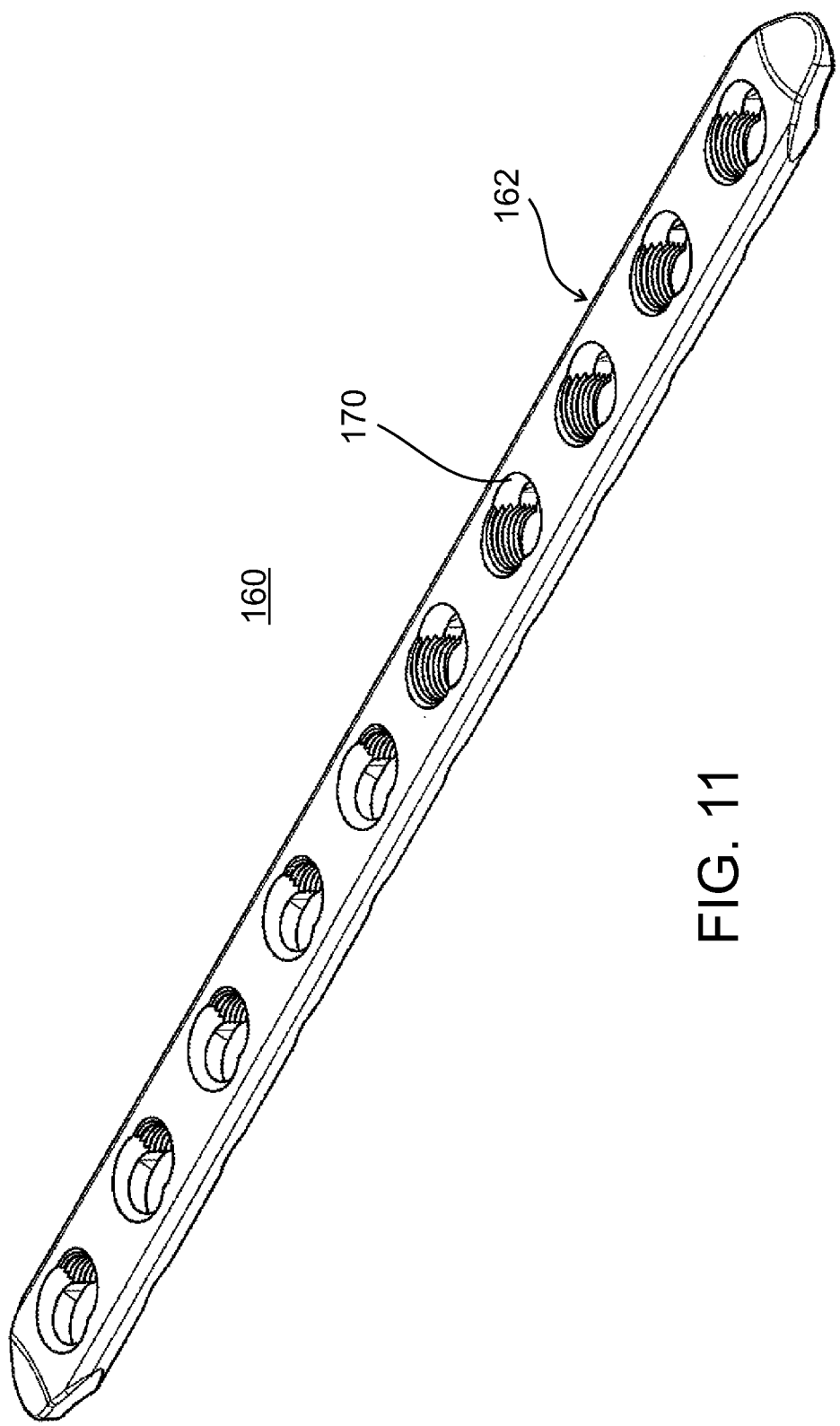
FIG. 11 is a schematic illustration of a bone plate.

FIG. 11 illustrates the construction of a bone plate 160 according to some embodiments of the invention. Plate 160 is comprised of a longitudinal fibers coated with one, two, three, four layers of ±45° longitudinal wires, longitudinal fibers coated by one, two, three, four layers of woven or braided ±45° layers. As an example, plate 160 is comprised of a woven or braided body 162 formed of substantially linearly extending comingled long carbon and polymer filaments in a thermoplastic polymer matrix as previously described. Passages 170 are provided to receive bone fixation screws (not shown). Optionally, passages 170 are formed in the molding process when plate 160 is fabricated. Alternatively, passages 170 are formed by machining after the plate has been fabricated.

Passages 170 may be threaded or non-threaded or a combination of the two. Optionally only a portion of some or all the passages are threaded with the other part is non-threaded, and designed to engage with the screw head.

According to some embodiments of the present invention, bone plate 160 is preformed based on average anatomical data, and then bent to a final shape before implantation based on specific anatomical data concerning the actual implant site for a particular patient. According to some exemplary embodiments, the final shaping is done by heating the preformed implant in a molding press with suitably shaped inserts. Force is applied to bend the plate to the required shape, and then the mold is cooled in a manner which allows the implant to retain its bent shape without substantial change in its other properties. As an example, a bone plate formed of carbon fibers, in a PEEK matrix, is heated to 380-400 Deg C, held at temperature for 5-30 minutes as needed to effect proper bending, then cooled at a rate of 5-30 Deg C per minute to 150 Deg C, and then cooled rapidly to room temperature.

Optionally, specific anatomical data for shaping plate 160 is obtained by direct measurement of the patient's implant site during a surgical procedure, or even visually. Alternatively, the specific anatomical data is obtained radiologically or by an MRI or by CT of the patient's implant site.

FIG. 12A-12D illustrate a bone fixation screw suitable for use with the various implant embodiments described above, or as standalone for fixation of fractures without an implant. The illustrated screws may be formed of the same fiber reinforced or self reinforcing polymer materials as described above.

As illustrated in FIG. 12A, the screws are comprised of a core 145 having long fibers extending in longitudinal direction, parallel to the screw axis 143 embedded in a polymer matrix. The thread 144 is made from composite material having long fibers, wound with the threads. Optionally some fibers may cross from the core and interweave into the thread as shown at 147, to increase the strength of the thread base 149.

Optionally, the thread 144 can be made of composite material with chopped fibers, optionally molded over the screw core.

The screw connector 148 for engagement with the closing and opening tool, may be of any conventional shape, for example, an internally or externally threaded hexagon, Phillips head, slotted, axial crown, and the like. Optionally the head of the screw may be a metal insert.

FIG. 12B illustrates a bone fixation screw 142a, having a helical composite material layer 150, preferably with long fibers directed in +/−45 deg relative to the axis 143. That layer may be included to add resistance to the torque applied on the screw during insertion or removal. Optionally layer 150 will comprise a winding only with one helical direction. Optionally the two fiber directions +/−45 deg are braided.

FIG. 12C illustrates a screw 142b providing added shear strength, by having metal shell 152 outside composite core 145. Shell 152 may be solid, and comprise the entire thread with no composite component. Such a structure provides the strength of the metal to resist shearing of the thread, and the strength of the composite core to resist bending. Optionally the distal end of the screw will be part of the shell 154, and optionally, may be self tapping.

FIG. 12D illustrates a screw 142c having the threads 144 coated with a thin layer 156 of titanium, or other metal such as titanium alloy Ti6Al4V, or any other biocompatible metal or metal alloy. The metal coating should be thick enough to provide the needed additional strength, but thin enough that it does not cause artifacts in CT images or MRIs. Coating thicknesses in the range of about 0.02 to 0.2 mm provide satisfactory results. As a specific example, the coating may have a thickness of a 0.1 mm.

The coating layer 156 may be formed in various ways including by electrochemical coating, physical vapor deposition, plasma spraying, molding the composite material into a metal shell etc. Whatever technique is employed, the coating should be made a smooth as possible, as a smooth surface is found to prevent attachment of re-grown tissue or bone to the threads, which would hinder removal of the screw if the implant must later be removed.

Optionally, bone screw can be made in any combination of the structural components described above.

Optionally, bone screw, in any combination can be canullated, with an internal lumen sized for use with guide wire.

Figure 13A:
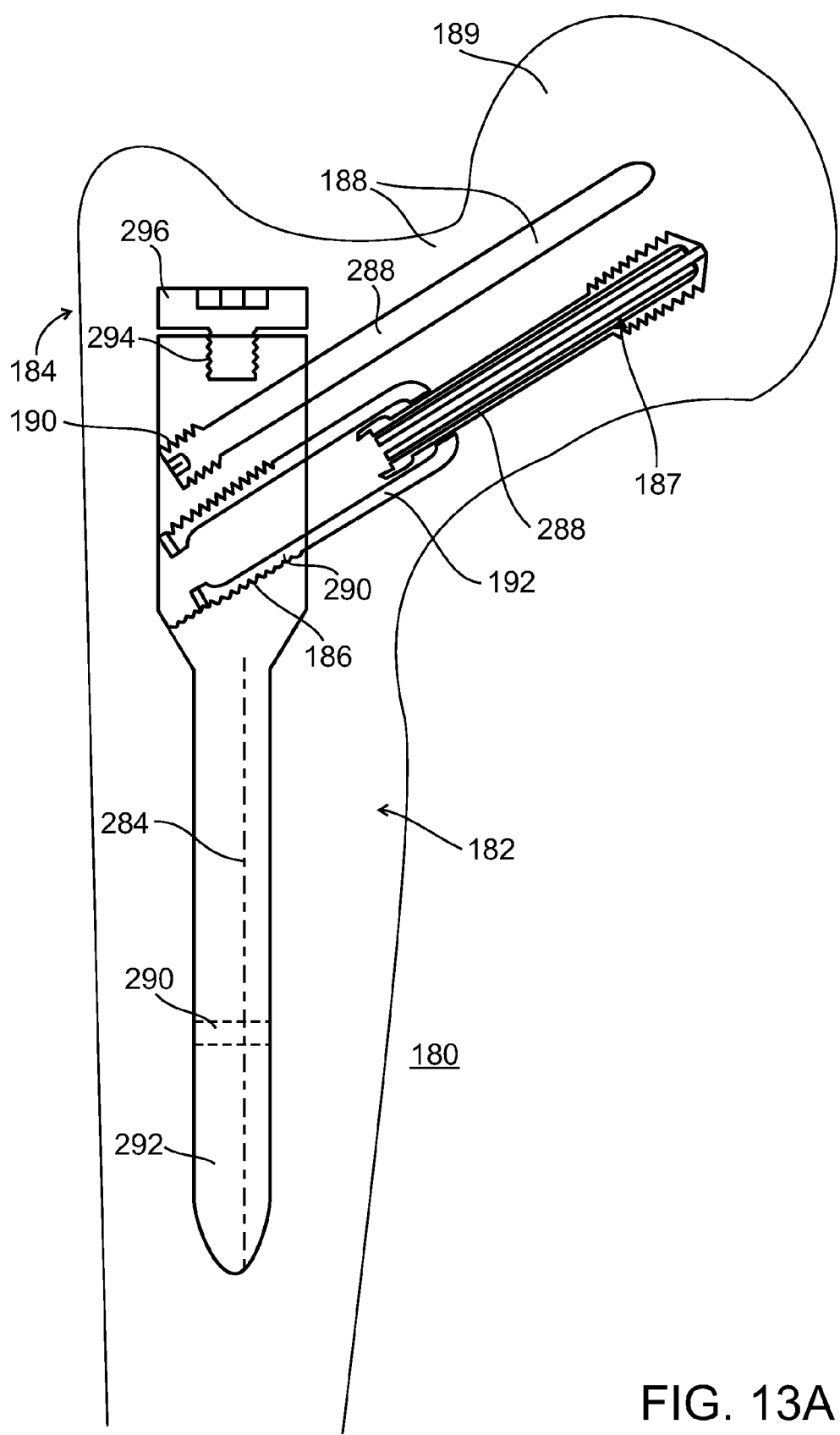
FIG. 13A illustrates a proximal femur (PF) nail, according to some embodiments of the invention.

FIG. 13A illustrates the construction of a proximal femur (PF) nail 180 formed of a reinforced polymer matrix, optionally including an embedded reinforcing insert as described above in connection with other embodiments of the invention. PF nails are used for repairing fractures involving the femur.

As illustrated, PF nail 180 includes an elongated stem 182 having a proximal end 184 with at least one passage 186 oriented at an angle to a longitudinal axis 284 of the nail. In use, passage 186 receives a proximal end bone fixation screw 286 which anchors the nail in the neck 188 and head 189 of the femur.

Optionally, PF nail 180 includes a threaded passage 190 to receive an anti-rotation pin 288. Passage 190 extends parallel to proximal end fixation screw passage 186.

Optionally, according to some exemplary embodiments of the invention, passage 186 is also threaded and receives a holder 192 within which leg screw 187 is slidingly received.

It should be understood that in addition to passages 186 and 190, a PF nail typically includes additional passages, such as passage 290 at a distal end 292. In use, passage 290 receives a bone fixation screw for anchoring PF nail 180 to a lower portion of the femur. Optionally other passages (not shown) may extend at an angle, for example, 90 degrees, to passage 290.

As in previously described embodiments, PF nail 180 may include radiopaque markings for some or all of the passages.

Optionally according to some exemplary embodiments of the invention, PF nail 180 includes an insertion tool connector 294 as described above, and an end cap 296 configured to be received in connector 294 after PF nail 180 has been implanted to prevent bone internal bone or tissue regrowth.

Figure 13B:
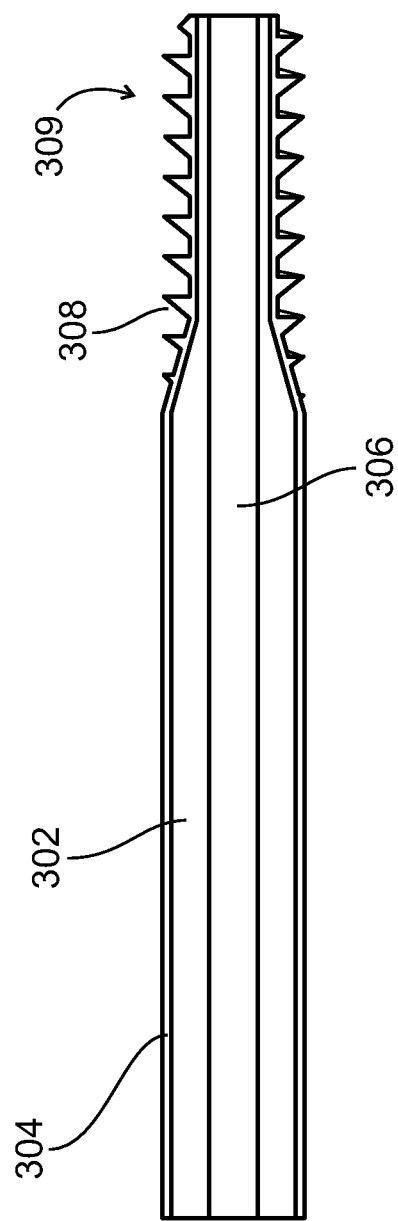
FIGS. 13B and 13C illustrate bone screws which may be used as leg screws with the PF nail of FIG. 13B, according to some embodiments of the invention.
Figure 13C:
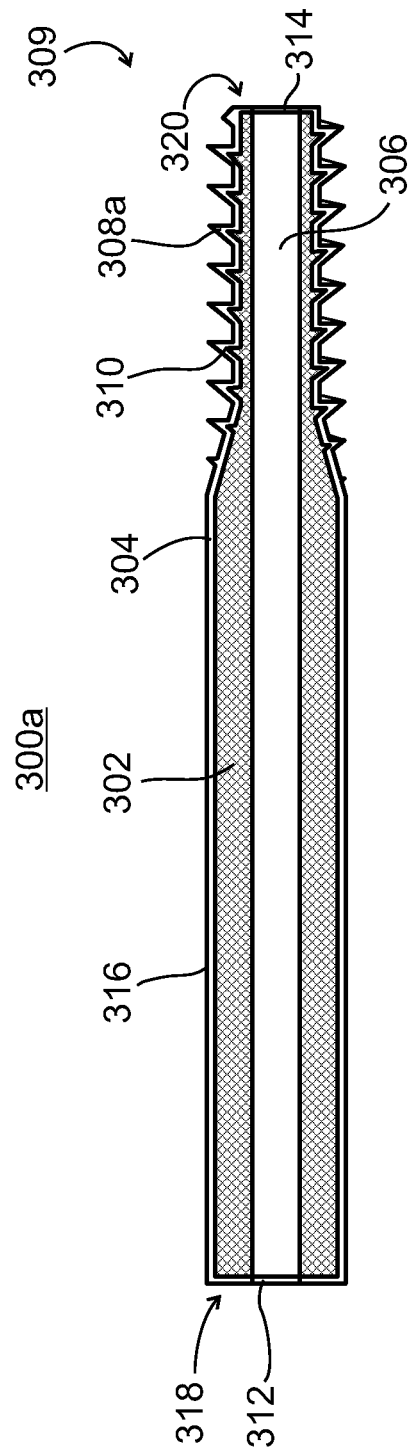

Exemplary embodiments of leg screws are shown in FIGS. 13B and 13C. Optionally, leg screws according to some embodiments of the invention, are formed of a core of the same composite material and the nail. Optionally, the screw is formed of metal, for example, a titanium alloy such as Ti-6Al-4V.

As shown in FIG. 13B, a leg screw 300 includes a reinforced polymer core 302, and a surrounding metal shell 304. Optionally, core 302 may include an internal lumen 306 intended to receive a guide wire (not shown) for assisting the surgeon during the implant procedure.

Shell 304 includes threads 308 at least at its distal end 309 for interlocking with the surrounding bone. Optionally, the threads are self tapping. Threads 308 may be formed only in shell 304 or may be internally relieved so that the polymer core 302 penetrates the threads, as best seen at 310 in FIG. 13C. In some instances, this may reduce the amount of metal in the shell for improved CT imaging and MRI visualization, and may help increase the strength of the connection between the screw core and the shell. The interface between the core and the shell may also include recesses and complementary projections of various shapes (not shown) to provide for stress sharing.

Optionally, as also illustrated in FIG. 13C, at 312 and 314, the metal shell 316 is crimped around proximal and distal ends 318 and 320 of polymer core 322.

Figure 14B:
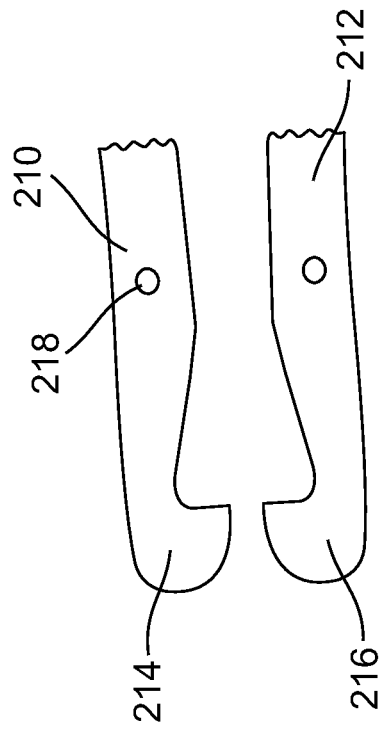
FIGS. 14A-14B show an implant removal tool according to some embodiments of the invention.
Figure 14A:
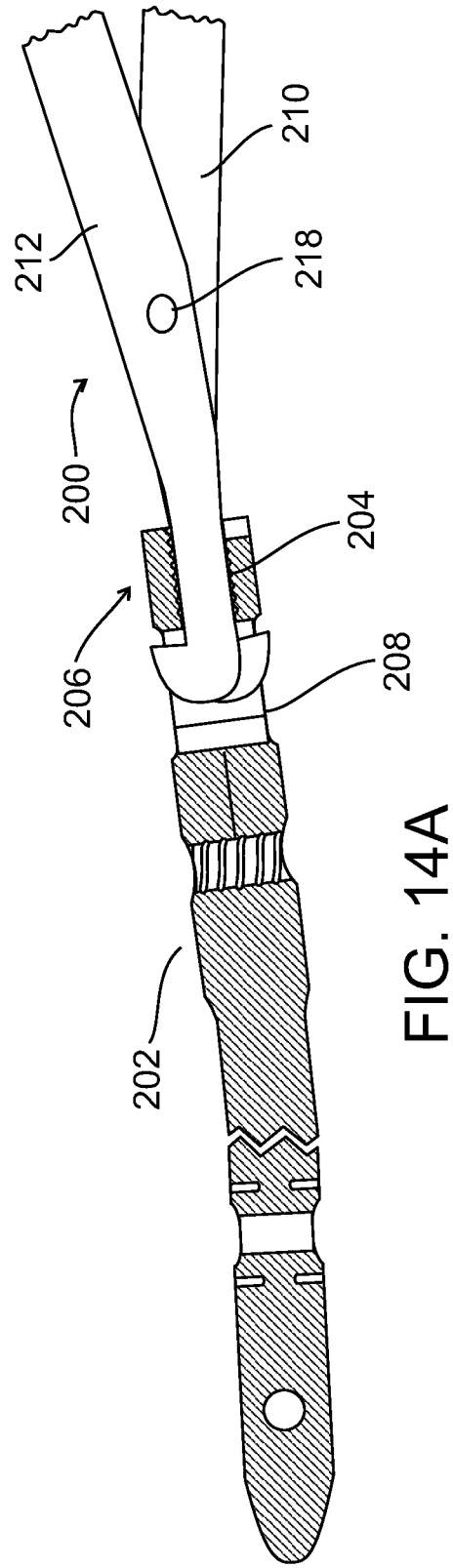

FIGS. 14A-14C show an implant removal tool 200 according to an aspect of some embodiments of the present invention. Removal tool 200 is configured to engage an installed implant 202 through the axial connector opening 204 at the proximal end 206 of the implant. For this purpose, axial opening 204 communicates with a transverse slot 208 as previously described.

As seen in FIG. 14B, tool 200 includes first and second arms 210 and 212, having respective transverse tips 214 and 216 at their distal end, and a suitable handle (not shown) for easy manipulation at their proximal ends. Arms 210 and 212 are connected by a pivot intermediate the proximal and distal ends and thus provide a scissor mechanism operable to move tips 214 and 216 between retracted and extended positions. In the retracted position, the tips are close to each other so that the distal end of tool 200 is easily insertable into opening 204. In the extended position, tips are separated, and engage the opposite sides of slot 208.

As will be understood, in the extended position axial, force can be applied to withdraw implant 202 from inside an opening in a bone.

Figure 15A:
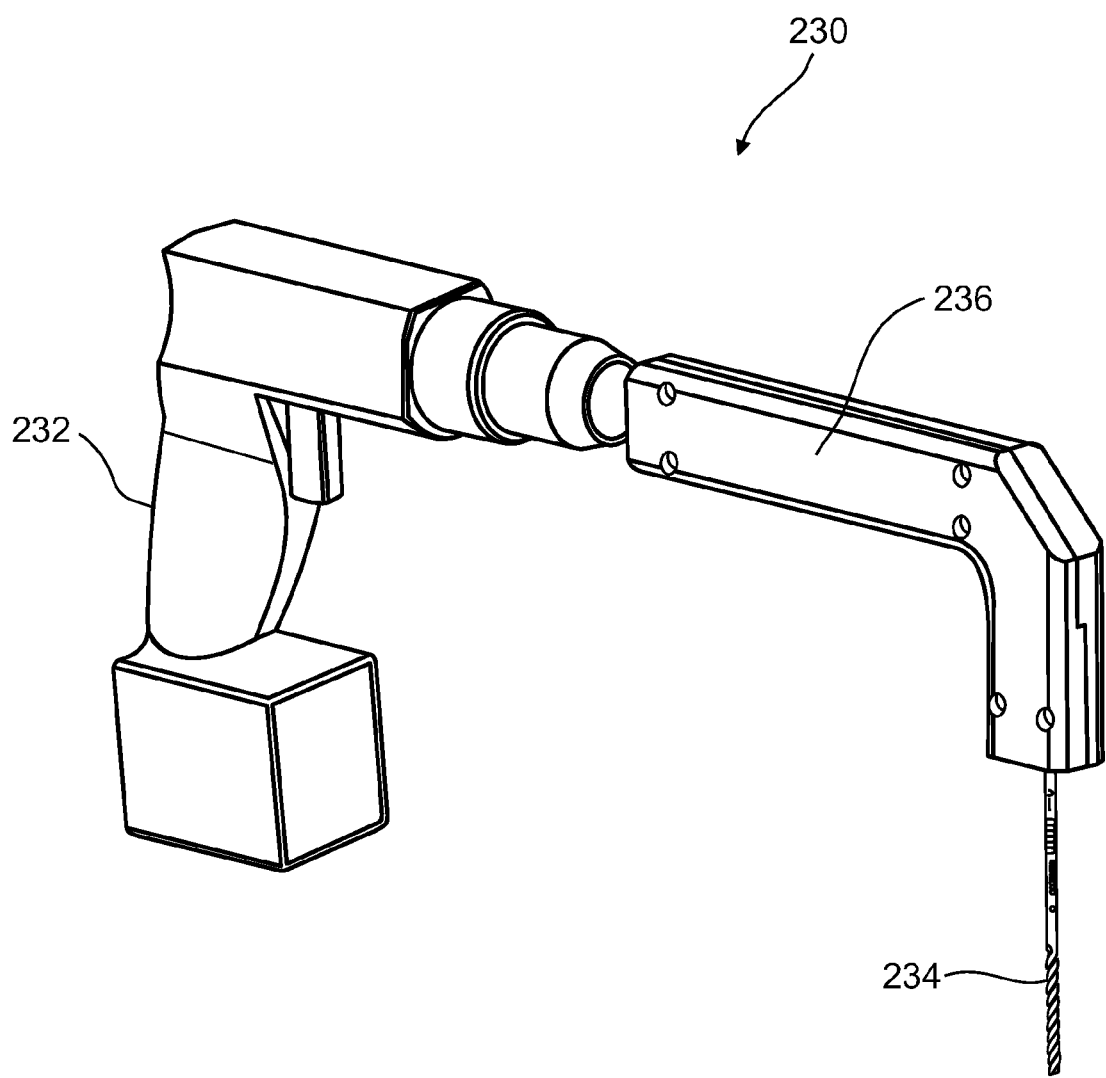
FIGS. 15A and 15B are schematic illustrations a bone drill and radiolucent connector that allows for unobstructed fluoroscopic visualization, according to some embodiments of the invention.
Figure 15B:
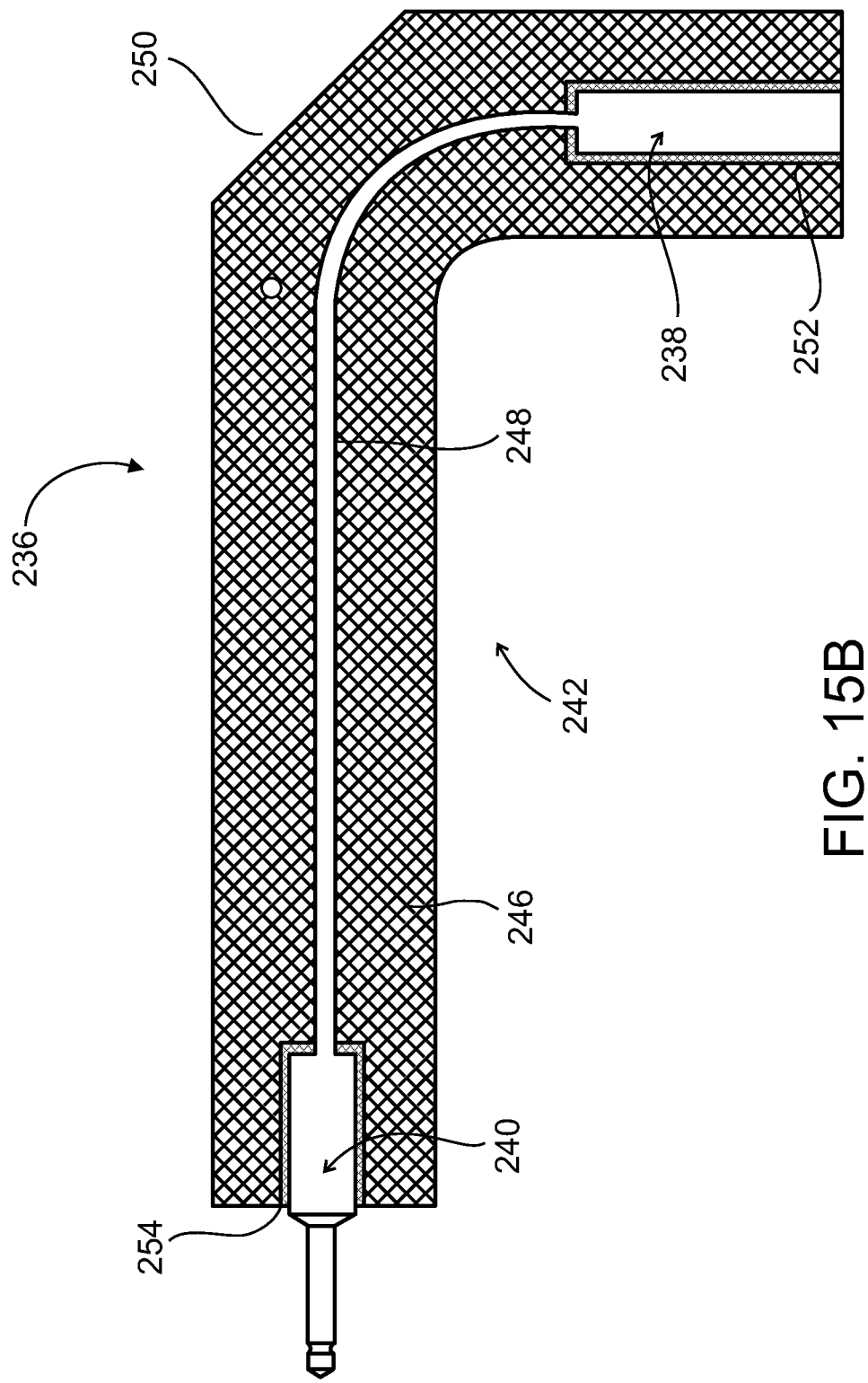
Figure 16C:
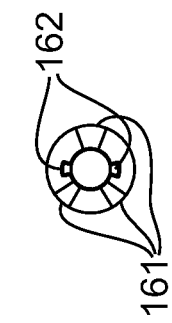
Figure 16A:
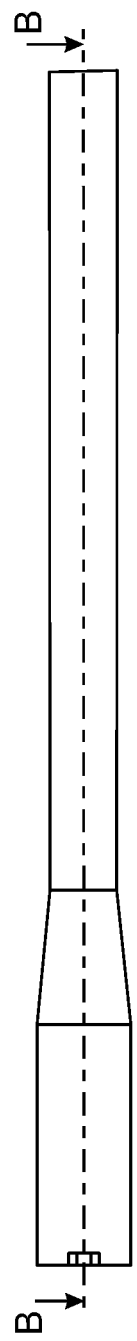
Figure 16B:
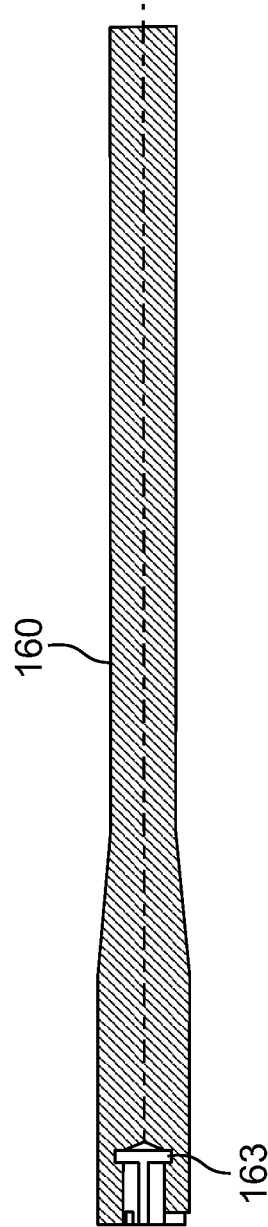

FIGS. 15A and 15B show a bone drilling assembly 230 used to prepare an implant site to receive a bone implant according to some embodiments of the invention. The illustrated construction is designed to minimize interference with fluoroscopic visualization of the drilling site by the surgeon.

Drilling assembly 230 includes a power unit 232 which drives a drill bit 234. An angled connector 236 is configured to be fitted between power unit 232 and drill bit 234. As best seen in FIG. 15B, connector 236 includes a female coupling 238 for connection to drill bit 234, and a male connector 240 for connection to power unit 232. These are mounted in a body 246 formed a polycarbonate or other suitable radiolucent material. A flexible cable 242 formed of for example multi-filaments of stainless steel or other suitable material is also mounted in body 246 and transfers torque from coupler 240 to coupler 238.

Still referring to FIG. 15B, connector 236 is angled at 250 so that couplers 238 and 240 are oriented, for example, at 90 degrees to each other. This allows power unit 232 to remain outside the fluoroscopy imaging range, and therefore does not interfere with visualization by the surgeon of the drilling site.

Couplers 238 and 240 are of conventional design, or of any other suitable and desired type. According to some embodiments, couplers 238 and 240 include outer sleeves 252 and 254 formed of Teflon or the like, which serve as bearings to minimize friction during rotation. Cable 242 is sized to rotate freely relative to the body 246 Optionally, instead of a flexible power transfer connection, rigid elongated rods connected together by suitable right-angle gear arrangement, may be employed. Preferably these parts are also formed of radiolucent material.

According to some embodiments, drill bit 234 may be made of a reinforced polymer matrix, optionally, including longitudinally extending reinforcing fibers as described above, coated with hard metal such as titanium, or diamond.

Power unit 230 may be a standard operating room drill. Optionally angled connector 234 may include a self-contained, electric motor, gear and battery, in that device, a separate power unit 232 is not needed.

Optionally, the connector 236 constructed is provided in sterile packaging, and is intended for disposal after a single use.

Optionally, as illustrated in FIGS. 16A-16G, the nail at the proximal end is connected to the insertion handle with a bayonet connection. Optionally, the proximal end nail includes longitudinal grooves 162 in order to insert the bayonet teeth 165 on the tube or rod 164 which connects the nail to the handle. Tube 164 rotates inside the nail in its radial groove 163. A nut 166 fastens over the tube 164 to tighten the nail to the handle. Optionally, the nail proximal end does not include longitudinal grooves for insertion of the bayonet teeth. Instead, tube 134 includes expandable bayonet teeth.

Figure 17A:
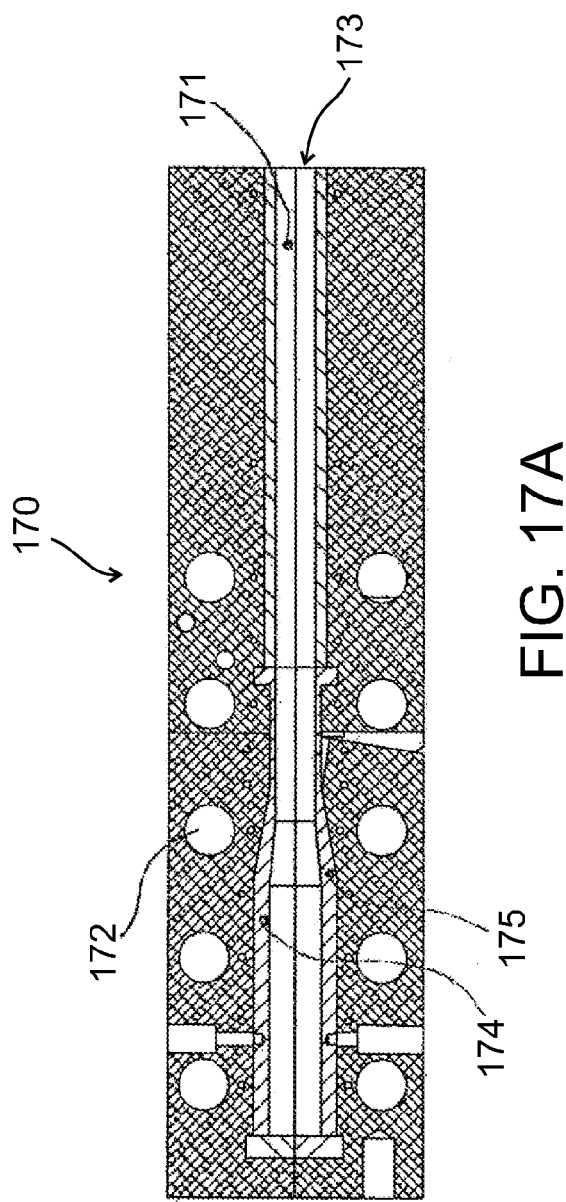
FIGS. 17A and 17B illustrate a tool for bending a bone nail to a desired configuration, according to some embodiments of the invention.
Figure 17B:
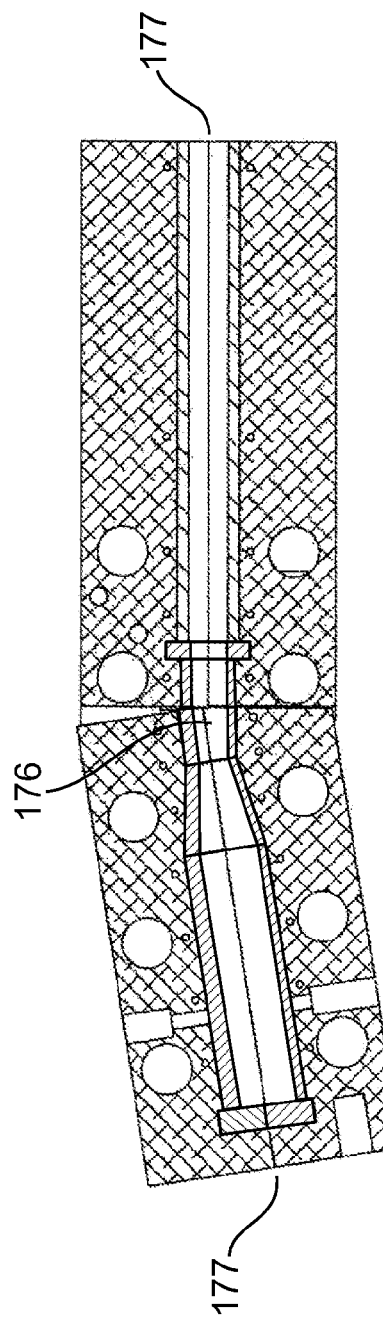

FIG. 17A and FIG. 17B illustrate a way to reduce cost during production of composite intramedullar nails. The nails are supplied in many lengths and diameters for humerus, tibia and femur bones, and are usually curved to follow the anatomic shape of the bones. However, it is less costly to manufacture straight nail, with all or most of the layers, and add a final manufacturing step of bending the nail.

FIG. 17A illustrates a bending tool 170. As shown, tool 170, includes a cavity 171 to receive a straight nail. The tool has electric heaters 172 heating the tool with the nail inside to a suitable plastic deformation temperature. For example for a nail formed of PEEK, a suitable temperature is in the range of 380 to 410 deg C. Optionally pressure may be applied to the nail during heating, for example by pressing the nail axially via opening 173. The tool has two halves 174 and 175 defining a mold cavity, made of material capable to bend without damage, at the process temperature, such as Nitinol.

At high temperature, the tool bends the nail. FIG. 17B illustrates the tool after bending. The nail is cooled within the tool, and the resulting curve 176 is retained.

PEEK and similar materials can be amorphous or crystalline to some degree, as determined by the desired heating and cooling treatment. Bending tool 170 has controller not shown, to establish the desired heating and cooling protocol.

After cooling, the tool opened along surface 177, and the curved nail is

Figure 18:
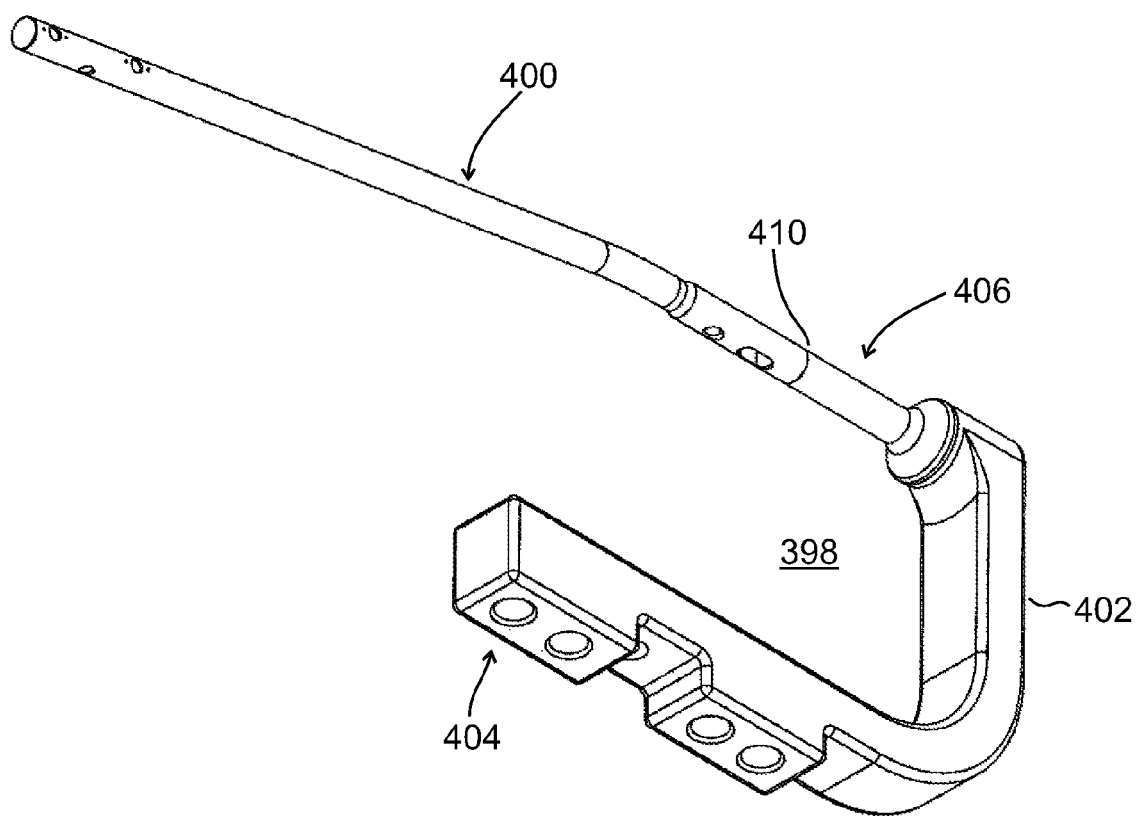
FIG. 18 shows an example of a drill guide and insertion tool for use with an implant, according to some of the implant embodiments.

FIG. 18 shows an example of a drill guide and insertion tool 398 for use with an implant 400 according to some of the implant embodiments as described above. As shown, tool 398 is comprised of a body 402 having a drill guide holes 404 and a coupling portion 406 which engages the coupler portion 410 of implant 400. Included in coupling portion 406 is an alignment element adapted to engage with a complementary element of the connector 410 to permit interconnection of the tool and the implant in the single orientation referred to in connection with FIGS. 4 and 5.

As various features of devices and methods have been described. It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

It should also be appreciated that some of the embodiments are described only as methods or only as apparatus, however the scope of the invention includes both methods for using apparatus and apparatus for applying methods. The scope of the invention also covers machines for creating the apparatus described herein. In addition, the scope of the invention also includes methods of using, constructing, calibrating and/or maintaining the apparatus described herein. When used in the following claims or in the text above, the terms "comprises", "comprising", "includes", "including" or the like mean "including but not limited."

What is claimed is:

1. An intramedullary nail, comprising:
    a cannulated body having a core constructed and configured to resist mainly bending loads, comprising substantially linearly extending long carbon fibers in a polymer matrix;
    a portion enclosing the core constructed and configured to resist mainly torsional loads, comprising multiple layers of carbon fibers in a polymer matrix, said fibers helically wound at about +45 degrees and −45 degrees with respect to a longitudinal axis of the nail;
    wherein said core comprises a thickness which is at least 10 times larger than a thickness of said portion enclosing the core.

2. The intramedullary nail according to claim 1, wherein an orientation of said helically wound fibers varies, so that the fibers are oriented at angles ranging between 35-55 degrees with respect to a longitudinal axis.

3. The intramedullary nail according to claim 1, wherein a diameter of a longitudinally extending inner lumen of said cannluated nail ranges between 2-2.9 mm, a diameter of said core comprised of linearly extending fibers ranges between 2.9-7 mm, and a diameter of said portion enclosing the core comprising helically wound filaments ranges between 7-11.6 mm.

4. The intramedullary nail according to claim 1, wherein said carbon fibers are braided to combine two neighbor layers.

5. The intramedullary nail according to claim 1, including a further layer surrounding the enclosing portion, said layer comprising linearly extending filaments.

6. The intramedullary nail according to claim 1, wherein said portion enclosing said core is coated by a layer comprising one or more of titanium and tantalum.

7. The intramedullary nail according to claim 1, wherein a proximal end is comprised of a further layer comprised of filaments in a circular spiral configuration.

8. The intramedullary nail according to claim 1, comprising at least one passage through said body, open at opposite ends, and configured to receive a bone fixation screw.

9. The intramedullary nail according to claim 8, comprising markings radiopaque to x-rays at opposite ends of the passage defining the location and orientation of the passage.

10. The intramedullary nail according to claim 9, wherein the markings are comprised of a plurality of localized areas of radiopaque material around the outside of the passage.

11. The intramedullary nail according to claim 9, wherein said radiopaque markings are in the form of rod-shaped elements located at each end of the passage.

12. The intramedullary nail according to claim 1, wherein a proximal end of said nail comprises a threaded bore.

13. The intramedullary nail according to claim 12, wherein said threaded bore is sized and shaped to receive an insertion tool, said tool comprising complementary external threads.

14. The intramedullary nail according to claim 12, wherein said threaded bore is sized and shaped for receiving an end cap, placed upon completion of the implantation.

15. The intramedullary nail according to claim 1, wherein said body is cannulated by said core comprising a substantially central, axially extending lumen.

16. The intramedullary nail according to claim 1, wherein a cumulative content of substantially linearly extending long carbon fibers of said intramedullary nail is at least two times higher than a cumulative content of said helically wound fibers.

17. The intramedullary nail according to claim 1, wherein a diameter of said core is up to 7.6 mm, and a thickness of said portion enclosing the core is between 0.3 mm and 0.6 mm.

* * * * *